(12) United States Patent
Seidel et al.

(10) Patent No.: US 7,195,920 B2
(45) Date of Patent: *Mar. 27, 2007

(54) COLLECTION SYSTEMS FOR CYTOMETER SORTING OF SPERM

(75) Inventors: George E. Seidel, LaPorte, CO (US); Lisa Herickhoff, Fort Collins, CO (US); John L. Schenk, Fort Collins, CO (US)

(73) Assignee: XY, Inc., Fort Collins, CO (US)

( * ) Notice: Subject to any disclaimer, the term of this patent is extended or adjusted under 35 U.S.C. 154(b) by 177 days.

This patent is subject to a terminal disclaimer.

(21) Appl. No.: 10/378,109

(22) Filed: Feb. 25, 2003

(65) Prior Publication Data

US 2003/0129091 A1    Jul. 10, 2003

Related U.S. Application Data

(62) Division of application No. 09/511,959, filed on Feb. 23, 2000, now Pat. No. 6,524,860, which is a division of application No. 09/001,394, filed on Dec. 31, 1997, now Pat. No. 6,149,867.

(51) Int. Cl.
*G01N 33/00* (2006.01)

(52) U.S. Cl. .................... 436/63; 436/10; 436/164; 422/73; 422/82.05; 209/571; 209/576

(58) Field of Classification Search ............ 422/68.1, 422/73, 82.05, 82.08, 82.09; 436/8, 10, 17–18, 436/63, 164, 172; 435/283.1, 287.1, 2, 6; 209/571, 576
See application file for complete search history.

(56) References Cited

U.S. PATENT DOCUMENTS

| | | | |
|---|---|---|---|
| 3,299,354 A | 1/1967 | Hogg | |
| 3,499,435 A | 3/1970 | Rockwell et al. | |
| 3,547,526 A | 12/1970 | Devereux | |
| 3,644,128 A | 2/1972 | Lipner | |
| 3,661,460 A | 5/1972 | Elking et al. | |
| 3,687,806 A | 8/1972 | Van den Bovenkamp | .... 195/1.3 |
| 3,710,933 A | 1/1973 | Fulwyler et al. | |
| 3,761,941 A | 9/1973 | Robertson | |
| 3,810,010 A | 5/1974 | Thom | |

(Continued)

FOREIGN PATENT DOCUMENTS

BR        9704313        6/1999

(Continued)

OTHER PUBLICATIONS

Webster's Ninth New Collegiate Dictionary, 1990, p. 137.*

(Continued)

*Primary Examiner*—Maureen M. Wallenhorst
(74) *Attorney, Agent, or Firm*—Santangelo Law Offices, P.C.

(57) ABSTRACT

Improved flow cytometer system particularly adapted to use for sex-selected sperm sorting include enhanced sheath fluid and other strategies which minimize stress on the sperm cells, including a 2.9 percent sodium citrate sheath solution for bovine species and a HEPES bovine gamete media for equine species. Improved collection systems and techniques for the process are described so that commercial applications of sperms samples as well as the resulting animals may be achieved.

3 Claims, 4 Drawing Sheets

U.S. PATENT DOCUMENTS

Figure 1:
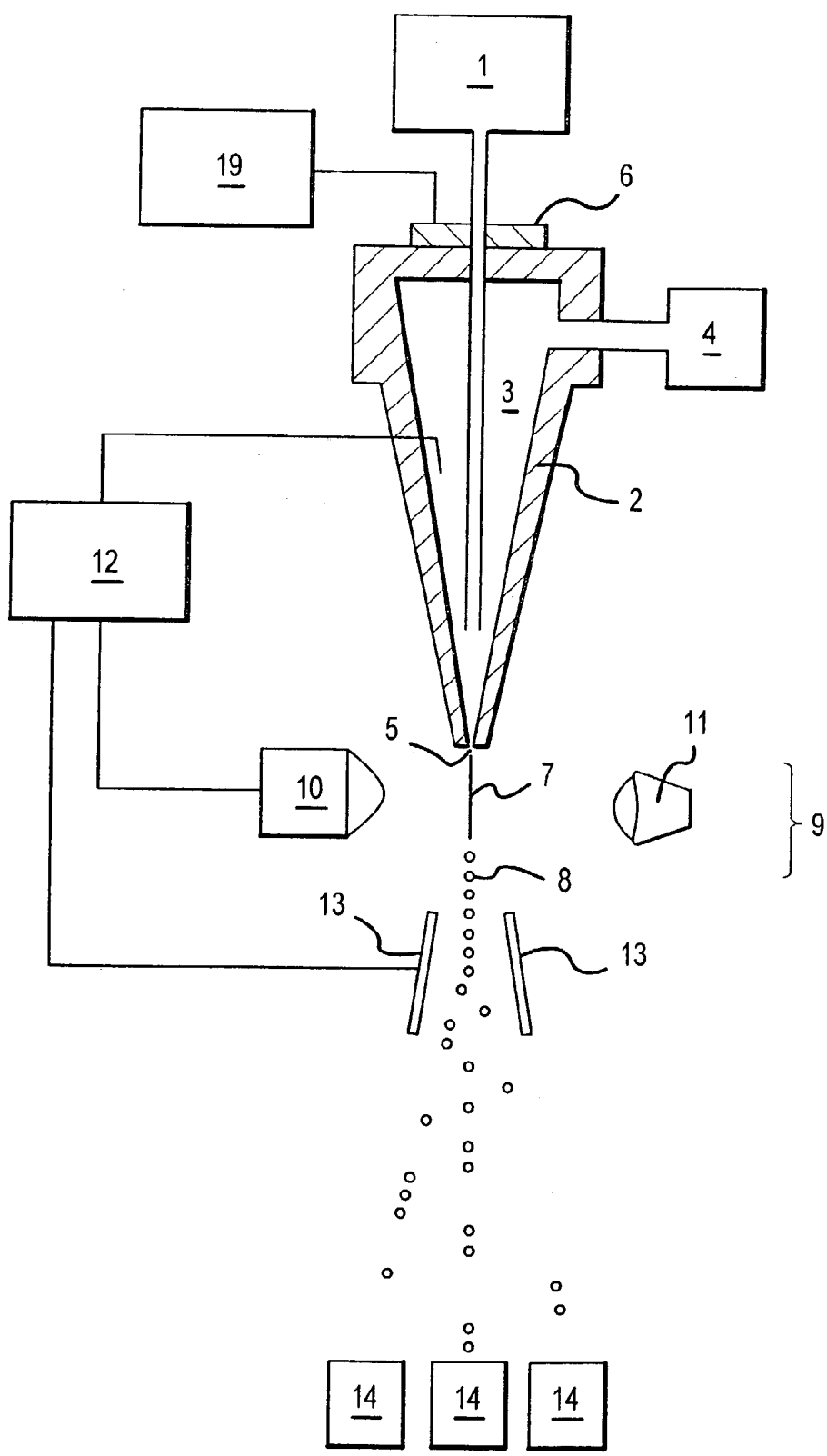

| | | |
|---|---|---|
| 3,826,364 A | 7/1974 | Bonner et al. |
| 3,829,216 A | 8/1974 | Persidsky ............... 356/36 |
| 3,833,796 A | 9/1974 | Fetner et al. |
| 3,877,430 A | 4/1975 | Wieder |
| 3,893,766 A | 7/1975 | Hogg |
| 3,894,529 A | 7/1975 | Shrimpton ............... 128/1 R |
| 3,909,744 A | 9/1975 | Wisner et al. |
| 3,947,093 A | 3/1976 | Goshima et al. |
| 3,960,449 A | 6/1976 | Carleton et al. |
| 3,963,606 A | 6/1976 | Hogg |
| 3,973,003 A | 8/1976 | Colas |
| 3,973,196 A | 8/1976 | Hogg |
| 4,007,087 A | 2/1977 | Ericsson |
| 4,009,260 A | 2/1977 | Ericsson ............... 424/105 |
| 4,014,611 A | 3/1977 | Simpson et al. |
| 4,067,965 A | 1/1978 | Bhattacharya ............... 424/105 |
| 4,070,617 A | 1/1978 | Kachel et al. |
| 4,083,957 A | 4/1978 | Lang ............... 424/78 |
| 4,085,205 A | 4/1978 | Hancock ............... 424/105 |
| 4,092,229 A | 5/1978 | Bhattacharya ............ 204/180 R |
| 4,155,831 A | 5/1979 | Bhattacharya ............ 207/299 R |
| 4,162,282 A | 7/1979 | Fulwyler et al. |
| 4,178,936 A | 12/1979 | Newcomb |
| 4,179,218 A | 12/1979 | Erdmann et al. |
| 4,191,749 A | 3/1980 | Bryant ............... 424/105 |
| 4,200,802 A | 4/1980 | Salzman et al. |
| 4,225,405 A | 9/1980 | Lawson ............... 204/180 R |
| 4,230,558 A | 10/1980 | Fulwyler |
| 4,255,021 A | 3/1981 | Brunsden |
| 4,267,268 A | 5/1981 | Nelson, Jr. |
| 4,274,408 A | 6/1981 | Nimrod |
| 4,274,740 A | 6/1981 | Eidenschink et al. |
| 4,276,139 A | 6/1981 | Lawson ............... 204/180 R |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,327,177 A | 4/1982 | Shrimpton |
| 4,339,434 A | 7/1982 | Ericsson ............... 424/105 |
| 4,341,471 A | 7/1982 | Hogg et al. |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair ............... 209/3.3 |
| 4,395,397 A | 7/1983 | Shapiro |
| 4,395,676 A | 7/1983 | Hollinger et al. |
| 4,400,764 A | 8/1983 | Kenyon |
| 4,422,761 A | 12/1983 | Frommer |
| 4,448,767 A | 5/1984 | Bryant ............... 424/85 |
| 4,474,875 A | 10/1984 | Shrimpton |
| 4,487,320 A | 12/1984 | Auer |
| 4,498,766 A | 2/1985 | Unterleitner |
| 4,501,366 A | 2/1985 | Thompson |
| 4,511,661 A | 4/1985 | Goldberg ............... 436/503 |
| 4,515,274 A | 5/1985 | Hollinger et al. |
| 4,523,809 A | 6/1985 | Toboada et al. |
| 4,538,733 A | 9/1985 | Hoffman |
| 4,559,309 A | 12/1985 | Evenson |
| 4,598,408 A | 7/1986 | O'Keefe |
| 4,600,302 A | 7/1986 | Sage, Jr. |
| 4,605,558 A | 8/1986 | Shrimpton |
| 4,631,483 A | 12/1986 | Proni et al. |
| 4,637,691 A | 1/1987 | Uehara et al. |
| RE32,350 E | 2/1987 | Bhattacharya ............ 204/180.1 |
| 4,654,025 A | 3/1987 | Cassou et al. |
| 4,660,971 A | 4/1987 | Sage et al. ............... 356/39 |
| 4,673,288 A | 6/1987 | Thomas et al. |
| 4,680,258 A | 7/1987 | Hammerling et al. ............ 435/7 |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. ............... 204/182.3 |
| 4,702,598 A | 10/1987 | Böhmer |
| 4,714,680 A | 12/1987 | Civin |
| 4,744,090 A | 5/1988 | Freiberg |
| 4,749,458 A | 6/1988 | Muroi et al. ............... 204/182.3 |
| 4,756,427 A | 7/1988 | Gohde et al. |
| 4,758,729 A | 7/1988 | Monnin |
| 4,764,013 A | 8/1988 | Johnston |
| 4,780,451 A | 10/1988 | Donaldson |
| 4,790,653 A | 12/1988 | North, Jr. |
| 4,794,086 A | 12/1988 | Kasper et al. |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,877,965 A | 10/1989 | Dandliker et al. |
| 4,942,305 A | 7/1990 | Sommer |
| 4,965,204 A | 10/1990 | Civin |
| 4,979,093 A | 12/1990 | Laine et al. |
| 4,980,277 A | 12/1990 | Junilla |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel ............... 435/30 |
| 4,999,283 A | 3/1991 | Zavos et al. ............... 435/2 |
| 5,005,981 A | 4/1991 | Schulte et al. |
| 5,007,732 A | 4/1991 | Ohki et al. |
| 5,021,244 A | 6/1991 | Spaulding ............... 424/561 |
| 5,030,002 A | 7/1991 | North, Jr. |
| 5,034,613 A | 7/1991 | Denk et al. |
| 5,055,393 A | 10/1991 | Kwoh et al. |
| 5,079,959 A | 1/1992 | Miyake et al. |
| 5,084,004 A | 1/1992 | Ranoux |
| 5,088,816 A | 2/1992 | Tomioka et al. |
| 5,098,657 A | 3/1992 | Blackford et al. |
| 5,101,978 A | 4/1992 | Marcus |
| 5,127,729 A | 7/1992 | Oetliker et al. |
| 5,132,548 A | 7/1992 | Borden et al. |
| 5,135,759 A | 8/1992 | Johnson ............... 424/561 |
| 5,144,224 A | 9/1992 | Larsen |
| 5,159,397 A | 10/1992 | Kosaka et al. |
| 5,159,403 A | 10/1992 | Kosaka |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,298,967 A | 3/1994 | Wells |
| 5,315,122 A | 5/1994 | Pinsky et al. |
| 5,346,990 A | 9/1994 | Spaulding ............... 530/350 |
| 5,359,907 A | 11/1994 | Baker et al. |
| 5,366,888 A | 11/1994 | Fry et al. |
| 5,367,474 A | 11/1994 | Auer et al. |
| 5,370,842 A | 12/1994 | Miyazaki et al. |
| 5,371,585 A | 12/1994 | Morgan et al. ............... 356/246 |
| 5,412,466 A | 5/1995 | Ogino |
| 5,437,987 A | 8/1995 | Ten et al. |
| 5,439,362 A | 8/1995 | Spaulding ............... 424/185.1 |
| 5,447,842 A * | 9/1995 | Simons ............... 435/6 |
| 5,452,054 A | 9/1995 | Dewa et al. |
| 5,461,145 A | 10/1995 | Kudo et al. |
| 5,466,572 A | 11/1995 | Sasaki et al. ............... 435/2 |
| 5,467,189 A | 11/1995 | Kreikebaum et al. |
| 5,471,294 A | 11/1995 | Ogino |
| 5,471,299 A | 11/1995 | Kaye et al. |
| 5,480,774 A | 1/1996 | Hew et al. |

| | | |
|---|---|---|
| 5,483,469 A | 1/1996 | Van den Engh et al. .... 364/555 |
| 5,494,795 A | 2/1996 | Guerry et al. |
| 5,496,272 A | 3/1996 | Chung et al. |
| 5,503,994 A | 4/1996 | Shear et al. |
| 5,514,537 A | 5/1996 | Chandler ........................ 435/2 |
| 5,523,573 A | 6/1996 | Hanninen et al. |
| 5,532,155 A | 7/1996 | Ranoux |
| 5,558,998 A | 9/1996 | Hammond et al. |
| 5,578,449 A | 11/1996 | Fr asch et al. |
| 5,589,457 A | 12/1996 | Wiltbank ..................... 514/12 |
| 5,596,401 A | 1/1997 | Kusuzawa |
| 5,601,235 A | 2/1997 | Booker et al. |
| 5,601,533 A | 2/1997 | Hancke et al. |
| 5,602,039 A | 2/1997 | Van den Engh ............ 436/164 |
| 5,602,349 A | 2/1997 | Van den Engh ......... 73/864.85 |
| 5,622,820 A | 4/1997 | Rossi |
| 5,641,457 A | 6/1997 | Vardanega |
| 5,650,847 A | 7/1997 | Maltsev et al. |
| 5,660,997 A | 8/1997 | Spaulding ................. 435/7.21 |
| 5,663,048 A | 9/1997 | Winkfein et al. |
| 5,672,880 A | 9/1997 | Kain |
| 5,675,401 A | 10/1997 | Wangler et al. |
| 5,684,575 A | 11/1997 | Steen |
| 5,687,727 A | 11/1997 | Kraus et al. |
| 5,690,895 A | 11/1997 | Matsumoto et al. .......... 422/73 |
| 5,691,133 A | 11/1997 | Critser et al. |
| 5,693,534 A | 12/1997 | Alak et al. |
| 5,700,692 A | 12/1997 | Sweet ......................... 436/50 |
| 5,707,808 A | 1/1998 | Roslaniec et al. |
| 5,708,868 A | 1/1998 | Ishikawa |
| 5,726,364 A | 3/1998 | Van den Engh ......... 73/864.85 |
| 5,759,767 A | 6/1998 | Lakowicz et al. |
| 5,777,732 A | 7/1998 | Hanninen et al. |
| 5,780,230 A | 7/1998 | Li et al. ........................ 435/6 |
| 5,786,560 A | 7/1998 | Tatah et al. |
| 5,793,485 A | 8/1998 | Gourley |
| 5,796,112 A | 8/1998 | Ichie |
| 5,804,436 A | 9/1998 | Okun et al. |
| 5,815,262 A | 9/1998 | Schrof et al. |
| 5,819,948 A | 10/1998 | Van den Engh |
| 5,824,269 A | 10/1998 | Kosaka et al. |
| 5,835,262 A | 11/1998 | Iketaki et al. |
| 5,868,767 A | 2/1999 | Farley et al. |
| 5,873,254 A | 2/1999 | Arav |
| 5,876,942 A | 3/1999 | Cheng et al. |
| 5,880,457 A | 3/1999 | Tomiyama et al. |
| 5,888,730 A | 3/1999 | Gray et al. |
| 5,891,734 A | 4/1999 | Gill et al. |
| 5,895,764 A | 4/1999 | Sklar et al. |
| 5,895,922 A | 4/1999 | Ho |
| 6,704,313 B1 | 4/1999 | De Resende et al. |
| 5,899,848 A | 5/1999 | Haubrich |
| 5,912,257 A | 6/1999 | Prasad et al. |
| 5,916,144 A | 6/1999 | Prather et al. |
| 5,916,449 A | 6/1999 | Ellwart et al. |
| 5,919,621 A | 7/1999 | Brown ........................... 435/6 |
| 5,985,216 A | 11/1999 | Rens et al. |
| 5,985,538 A | 11/1999 | Stachecju |
| 6,002,471 A | 12/1999 | Quake |
| 6,050,935 A | 4/2000 | Ranoux et al. |
| 6,071,689 A | 6/2000 | Seidel et al. .................... 435/2 |
| 6,087,352 A | 7/2000 | Trout |
| 6,117,068 A | 9/2000 | Gourley et al. |
| 6,119,465 A | 9/2000 | Mullens et al. |
| 6,133,044 A | 10/2000 | Van den Engh |
| 6,140,121 A | 10/2000 | Ellington et al. |
| 6,149,867 A * | 11/2000 | Seidel et al. .................. 422/73 |
| 6,153,373 A | 11/2000 | Benjamin et al. |
| 6,154,276 A | 11/2000 | Mariella, Jr. |
| 6,175,409 B1 | 1/2001 | Nielsen et al. |
| 6,177,277 B1 | 1/2001 | Soini |
| 6,238,920 B1 | 5/2001 | Nagai et al. |
| 6,248,590 B1 | 6/2001 | Malachowski |
| 6,263,745 B1 | 7/2001 | Buchanan et al. |
| 6,283,920 B1 | 9/2001 | Eberle et al. |
| 6,357,307 B2 | 3/2002 | Buchanan et al. |
| 6,395,305 B1 | 5/2002 | Buhr et al. |
| 6,411,835 B1 | 6/2002 | Modell et al. |
| 6,463,314 B1 | 10/2002 | Haruna |
| 6,489,092 B1 | 12/2002 | Benjamin et al. |
| 6,524,860 B1 * | 2/2003 | Seidel et al. ................... 436/63 |
| 6,528,802 B1 | 3/2003 | Karsten et al. |
| 6,534,308 B1 | 3/2003 | Palsson et al. |
| 6,537,829 B1 | 3/2003 | Zarling et al. |
| 6,577,387 B2 | 6/2003 | Ross, III et al. |
| 6,590,911 B1 | 7/2003 | Spinelli et al. |
| 6,604,435 B2 | 8/2003 | Buchanan et al. |
| 6,617,107 B1 | 9/2003 | Dean |
| 6,618,679 B2 | 9/2003 | Loehrlein et al. |
| 6,642,018 B1 | 11/2003 | Koller et al. |
| 6,667,830 B1 | 12/2003 | Iketaki et al. |
| 6,671,044 B2 | 12/2003 | Ortyn et al. |
| 6,673,095 B2 | 1/2004 | Nordquist |
| 6,782,768 B2 | 8/2004 | Buchanan et al. |
| 6,819,411 B1 | 11/2004 | Sharpe et al. |
| 2002/0096123 A1 | 7/2002 | Whittier et al. |
| 2002/0113965 A1 | 8/2002 | Roche et al. |
| 2002/0119558 A1 | 8/2002 | Seidel et al. |
| 2002/0141902 A1 | 10/2002 | Ozasa et al. |
| 2002/0186375 A1 | 12/2002 | Asbury et al. |
| 2003/0098421 A1 | 5/2003 | Ho |
| 2003/0129091 A1 | 7/2003 | Seidel et al. |
| 2003/0157475 A1 | 8/2003 | Schenk |
| 2003/0207461 A1 | 11/2003 | Bell et al. |
| 2003/0209059 A1 | 11/2003 | Kawano |
| 2004/0005582 A1 | 1/2004 | Shipwast |
| 2004/0031071 A1 | 2/2004 | Morris et al. |
| 2004/0049801 A1 | 3/2004 | Seidel |
| 2004/0053243 A1 | 3/2004 | Evans |
| 2004/0055030 A1 | 3/2004 | Maxwell et al. |
| 2004/0062685 A1 | 4/2004 | Norton et al. |
| 2004/0132001 A1 | 7/2004 | Seidel et al. |
| 2005/0003472 A1 | 1/2005 | Muhammad |
| 2005/0112541 A1 | 5/2005 | Durack |
| 2005/0214733 A1 | 9/2005 | Graham |

FOREIGN PATENT DOCUMENTS

| | | |
|---|---|---|
| DE | 69028526 | 2/1997 |
| DE | 195 49 015 C1 | 4/1997 |
| DE | 198 82 943.3 | 2/2001 |
| EP | 0025296 A2 | 3/1981 |
| EP | 0071538 A1 | 2/1983 |
| EP | 0160201 A2 | 11/1985 |
| EP | 0189702 A1 | 8/1986 |
| EP | 0 276 166 | 1/1988 |
| EP | 0288029 B1 | 4/1988 |
| EP | A-0 366794 | 5/1990 |
| EP | 0461618 | 12/1991 |
| EP | 0468100 A1 | 1/1992 |
| EP | 0570102 A1 | 3/1993 |
| EP | 0538786 A | 4/1993 |
| EP | 606847 A2 | 7/1994 |
| EP | A-0 478155 | 1/1998 |
| EP | 0781985 A3 | 7/1998 |
| EP | 1250897 A1 | 10/2002 |
| EP | 1403633 A3 | 4/2004 |
| FR | 2574656 A1 | 6/1986 |
| FR | A-2 635453 | 2/1990 |
| FR | 2 647 668 A | 12/1990 |
| FR | 2699678 A1 | 6/1994 |
| JP | 61139747 (A) | 6/1986 |
| JP | 61159135 (A) | 7/1986 |
| JP | 2024535 | 1/1990 |
| JP | 4126064 (A) | 4/1992 |
| JP | 4126065 (A) | 4/1992 |

| | | |
|---|---|---|
| JP | 4126066 (A) | 4/1992 |
| JP | 4126079 (A) | 4/1992 |
| JP | 4126080 (A) | 4/1992 |
| JP | 4126081 (A) | 4/1992 |
| SU | 1056008 | 11/1983 |
| SU | 1260778 A1 | 9/1986 |
| WO | WO 88/07198 | 9/1988 |
| WO | WO 90/13315 | 11/1990 |
| WO | WO 90/13315 A1 | 11/1990 |
| WO | WO 96/12171 | 10/1995 |
| WO | WO 96/31764 | 10/1996 |
| WO | WO 98/34094 | 6/1998 |
| WO | WO 99/05504 | 7/1998 |
| WO | WO 98/48259 | 10/1998 |
| WO | WO 99/38883 | 5/1999 |
| WO | WO 99/33956 | 7/1999 |
| WO | WO 99/33956 | 8/1999 |
| WO | WO 99/42810 | 8/1999 |
| WO | WO 99/44037 A1 | 9/1999 |
| WO | WO 00/06193 | 10/2000 |
| WO | WO 01/37655 A1 | 5/2001 |
| WO | WO 01/40765 A2 | 6/2001 |
| WO | WO 01/40765 A3 | 6/2001 |
| WO | WO 01/51612 A1 | 7/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/19943 A1 | 3/2002 |
| WO | WO 02119943 A1 | 3/2002 |
| WO | WO 02/28311 A2 | 4/2002 |
| WO | WO 02/41906 A2 | 5/2002 |
| WO | WO 02/43486 A1 | 6/2002 |
| WO | WO 02/43574 A2 | 6/2002 |
| WO | WO 04/009237 A1 | 1/2004 |
| WO | WO 04/009237 A3 | 1/2004 |
| WO | WO 04/012837 A1 | 2/2004 |
| WO | WO 04/012837 A3 | 2/2004 |
| WO | WO 04/017041 A2 | 2/2004 |
| WO | WO 04/017041 A3 | 2/2004 |
| WO | WO 04/024227 A2 | 3/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 04/104178 A2 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |

OTHER PUBLICATIONS

Abdel-Ghaffar, A.E., et al., "Rabbit Semen Metabolism", Dept. of Theriogenology, Fac. of Vet Med., Dept. of Biochemistry, Zagazig University, Zagazig, Egypt, pp. 305-312 (1994).

Cran, D.G., et al., "The predetermination of embryonic sec using flow cytometrically separated X and Y spermatozoa", Human Reproduction Update (1996), vol. 2, No. 4 pp. 355-363.

Gourley, D.D., et al., "Laparoscopic Artificial Insemination in Sheep", Veterinary Clinics of North America: Food Animal practice, vol. 6, No. 3, Nov. 1990, pp. 615-633.

Iwazumi, Yasuaki, et al., "Superovulation Using CIDR® in Holstein Cows", Journal of Reproduction and Development, vol. 40, No. 3 (1994), pp. 259-266.

Maxwell, W.M.C., et al., "Viability and Membrane Integrity of Spermatozoa after Dilution and Flow Cytometric Sorting in the Presence or Absence of Seminal Plasma", Reprod. Fertil. Dev. (1997), vol. 8, pp. 1165-1178.

Patterson, D.J. et al., Estrus Synchronization with an Oral Progestogen Prior to Superovulation of Postpartum Beef Cows., Theriogenology 48:1025-1033 (197).

Schiewe, et al., "Transferable Embryo Recovery Rates following Different Insemination Schedules in Superovulated Beef Cattle", Theriogenology (1987) vol. 28, No. 4 pp. 395-406.

Swenson, S.L., et al., "PRRS virus infection in boars: isolation from semen and effect on semen quality", From the 1995 Research Investment Report, Iowa State University, Veterinary Clinical Sciences, Iowa State University.

http://www.cytomation.com/products/moflo_sorters_index.html., MoFlo® High-Performance Cell Sorter, pp. 1-2, printed Apr. 29, 2003.

"Capacitation of Bovine Sperm by Heparin," J.J. Parrish, J. Susko-Parrish, M.A. Winer, and N.L. First, Department of Meat and Animal Science, University of Wisconsin, Madison, WI 53706, Biology Of Reproduction 38, 1988, pp. 1171-1180.

"Insemination of Holstein Heifers With Very Low Numbers Of Unfrozen Spermatozoa." G.E. Seidel, Jr., C.H. Allen, Z. Brink, J.K. Graham, and M.B. Cattell, Colorado State University, Fort Collins, Atlantic Breeders Cooperative, Lancaster, PA., DUO Dairy, Loveland, CO. Jul. 1995.

"Prospects For Sexing Mammalian Sperm," Colorado Associated University Press, Animal Reproduction Laboratory College of Veterinary Medicine and Biomedical Sciences, Colorado State University, Fort Collins, CO, 80523 Edited by Rupert P. Amann and George E. Seidel, Jr., 1982.

"Prostaglandin F2a—A Fertility Drug In Dairy Cattle?", K.L. Macmillan and A.M. Day, Ruakura Animal Research Station, Private Bag, Hamilton, New Zealand, Theriogenology, Sep. 1982, vol. 18 No. 3, pp. 245-253.

"Uterine Horn Insemination of Heifers With Very Low Numbers of Nonfrozen and Sexed Spermatozoa," G.E. Seidel, Jr., C.H. Allen, L.A. Johnson, M.D. Holland, Z. Brink, G.R. Welch, J.K. Graham and M.B. Cattell, Animal Reproduction and Biotechnology Laboratory Colorado State University, Atlantic Breeders Cooperative, Lancaster, PA 17601, Germplasm and Gamete Physiology Laboratory ARS, USDA, Beltsville, MD 20705, DUO Diary, Loveland, CO 80538, Theriogenology 48: 1255-1264, 1997.

Blanchard, T. and Dickson, V., Stallion Management, The Veterinary Clinics of North America, Equine Practice, vol. 8, No. 1, Apr. 1992, pp. 207-218.

Catt, et al., "Assesment of Ram and Boar Spermatozoa During Cell-Sorting by Flow Cytometry", Reproduction Dom Animal, vol. 32, 1997, pp. 251-258.

D.G. Cran, W.A.C. McKelvey, M.E. King, D.F. Dolman, T.G. McEvoy, P.J. Broadbent and J.J. Robinson, Mastercalf, Craibstone"Production of Lambs by Low Dose Intrauterine Insemination With Flow Cytometrically Sorted and Unsorted Semen,", Bucksbum, Aberdeen, AB21 9TN, UK Scottish Agricultural College, Craibstone, Bucksbum, Aberdeen. AB21 9YA, UK, Theriogenology, p. 267, date unknown.

Hawk, H.W., et al., "Fertilization Rates in Superovulating Cows After Deposition of Semen on the Infundibulum Near the Uterotubal Junction or After Insemination with High Numbers of Sperm", XP-002103478, Theriogenology, May 1988, vol. 29, No. 5, pp. 1131-1142.

Jafar, etal., "Sex Selection in Mammals: A Review", Theriogenology, vol. 46, 1996, pp. 191-200.

Johnson, L.A., et al., "Sex Preselection in Rabbits: Live Births from X and Y Sperm Separated by DNA and Cell Sorting", Execptional Paper-Rapid Publication, XP-002103476, Biology of Reproduction 41, 199-203, 1989, pp. 199-203.

Johnson, L.A., and Pinkel, D., "Modification of a Laser-Based flow Cytometer for High-Resolution DNA Analysis of Mammalian Spermatozoa", Cytometry 7, 1986, pp. 268-273.

Johnson, "Gender preselection in Mammals: An overview", Dtsch. tierarztl. Wschr, vol. 103, Aug./Sep. 1996, pp. 288-291.

Karabinus, et al., "Effects of Egg Yolk-Citrate and Milk Extenders on Chromatin Structured Viability of Cryopreserved Bull Sperm", Journal of Dairy Science, vol. 74, No. 11, 1999, pp. 3836-3848.

McKinnin, A. and Voss, J., "Equine Reproduction", Lea & Febiger, Philadelphia, 1993, pp. 291, 299-302, 345-348, 739-797.

McNutt, et al., "Flow Cytometric Sorting of Sperm: Influence on Fertilization and Embryo/Fetal Development in the Rabbits", Molecular Reproduction and Development, vol. 43, 1996, pp. 261-267.

Meinert, C., et al., "Advancing the time of ovulation in the mare with a short-term inplant releasing the GnRH analogue deslorelin", Equine Veterinary Journal, 25, 1993, pp. 65-68.

Nowshari, et al., Theriogenology, vol. 43, 1995, pp. 797-802.

Parent U.S. Appl. No. 09/001,394, entitled "Sheath Fluids and Collection Systems for Sex-Specific Cytometer Sorting of Sperm", filed on Dec. 31, 1997, 87 total pages which includes four drawings.

Pickett, B.W., and Shiner, K.A., "Recent developments in artificial insemination in horses", Livestock Production Science, 40, 1994, pp. 31-36.

Pinkel, D., et al, "Flow Cytometric Determination of the Proportions of X- and Y Chromosome-Bearing Sperm in Samples of Purportedly Separated Bull Sperm", Journal of Animal Science, vol. 60, No. 5, 1985, pp. 1303-1307.

Rath, D., et al., "Production of Piglets Preselected for Sex Following in Vitro Fertilization with X and Y Chromosome-Bearing Spermatozoa Sorted by Flow Cytometry", Theriogenology, 47, 1997, pp. 795-800.

Seidel, G.E. et al, "Artificial Insemination With X-and Y-Bearing Bovine Sperm", Animal Reproduction and Biotechnology Laboratory, Colorado State University, Fort Collins, CO; Germplasm and Gamete Physiology Lab, ARS, USDA, Beltsville, MD; Atlantic Breeders Coop, Lancaster, PA; Duo Diary, Loveland, CO, USA Jan. 1996.

Seidel, G.E., et al, "Insemination Of Heifers With Very Low Numbers Of Frozen Spermatozoa", Colorado State University, Fort Collins, Atlantic Breeders Cooperative, Lancaster, PA, DUO Dairy, Loveland, CO, Jul. 1996.

Squires, E., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, Apr. 1996, pp. 127-130.

Vazquez, J. et al., "Nonsurgical Uterotubal Insemination in the Mare", Proceedings of the 44th Annual Convention of the American Association of Equine Practitioners, Baltimore, Maryland, Dec. 6-9, 1998, vol. 44, pp. 68-69.

Welch, G., et al., "Flow Cytometric Sperm Sorting and PCR to Confirm Separation of X- and Y- Chromosome Bearing Bovine Sperm", Animal Biotechnology, 6 (2), 131-139, 1995, pp. 131-139.

XP-002103478, File Biosis, 1988, one page.

Amoah, E.A. and Gelaye, S. 1996. Biotechnological advances in goat reproduction. J. Anim. Sci. 75(2):578-585.

Andersen, V.K., Aamdal, J. and Fougner, J.A. 1973. Intrauterine und tiefzervikale Insemination mit Gefriersperma bein Schat. Zuchthygiene. 8:113-118.

Baker, R.D., Dziuk, P.J. and Norton, H.W. 1968. Effect of volume of semen, number of sperm and drugs on transport of sperm in artificially inseminated gilts. J. Anim. Sci. 27:88-93.

Becker, S.E. and Johnson, A.L. 1992. Effects of gonadotropin releasing hormone infused in a pulsatite or continuous fashion on serum gonadotropin concentrations and ovulation in the mare. J. Anim. Sci. 70:1208-1215.

Bedford, S .J. and Hinrichs, K. 1994. The effect of insemination volume on pregnancy rates of pony mares. Theriogenology 42:571-578.

Berger, G.S. 1987. Intratubal insemination. Fert. Steril. 48:328-330.

Beyhan, Z., Welch, G.R. and First, N.L. 1998. Sexual dimorphism in IVF bovine embryos produced by sperm sorted by high speed flow cytometry. Theriogenology. 49(1):359. abstr.

Bracher, V. and Allen, W.R., A Videoendoscopic Examination of the Mare=s Uterus: Findings in Normal Fertile Mares@, Equine Veterinary Journal, vol. 24 (1992), pp. 274-278.

Braselton, W.E. and McShan, W.H. 1970. Purification and properties of follicle stimulating and luteinizing hormones from horse pituitary glands. Arch. Biochem. Biophys. 139:45-48.

Brethour, J.R. and Jaeger, J.R., "The Single Calf Heifer System", Kansas Agric. Sta. Rep of Progress 570, 1989.

Bristol, S.P. 1982. Breeding behavior of a stallion at pasture with 20 mares in synchronized oestrus. J. Reprod. Fert. Suppl. 32:71.

Buchanan, B.R., et al, AInsemination of Mares with Low Numbers of Either Unsexed or Sexed Spermatozoa@, Theriogenology, vol. 53, pp. 1333-1344, (2000).

Burwash, L.D., Pickett, B.W., Voss, J.L. and Back, D.G. 1974. Relatioship of duration of estms to pregnancy rate in normally cycling, non-lactating mares. J.A.V.M.A. 165:714-716.

Caslick, E.A., A The Vulva and the Vulvo-vaginal Orifice and its Relation to Genital Health of the Thoroughbred MareA, Cornell Veterinarian, vol. 27, 1937, pp. 178-187.

Chin, W.W. and Boime, I. 1990. In: Glycoprotein Hormones. Serona Symp. Norwell, MA. pp. 19-20.

Chung, Y.G., Schenk, J.L., Herickhoff, L.A. and Seidel, G.E. Jr. 1998. Artificial insemination of superovulated heifers with 600,000 sexed sperm. J Anim. Sci. Suppl. 1. 836:215. abstr.

Clement, F., Vincent, P., Mahla, R., Meriaux, J.C. and Palmer, E. 1998. Which insemination fertilizes when several successive inseminations are performed before ovulation. $7^{th}$ Int. Symp. Eq. Repro. 151. abstr.

Cran, D.G., Johnson, L.A., Miller, N.G., Cochrane, D. and Polge, C. 1993. Production of bovine calv.es following separation of X- and Y-chromosome bearing sperm and *in vitro* fertilisation. Vet. Rec. 132:40-41.

Curran, S. 1998. In: Equine Diagnostic Ultrasonography. Fetal gender determination. Rantanen & McKinnon. $1^{st}$ Ed. Williams and Wilkins. pp. 165-169.

Day, B.N., Abeydeera, L.R., Johnson, L.A., Welch, G.R., Wang, W.H., Cantley, T.C. and Rieke, A. 1998. Birth of piglets preselected for gender following invitro fertilization of in vitro matured pig oocytes by X and Y bearing spermatozoa sorted by high speed flow cytometry. Theriogenology. 49(1):360. abstr.

Dean, P.N., Pinkel, D. and Mendelsob. n, M.L. 1978. Hydrodynamic orientation of spermatozoa heads for flow cytometry. Biophys. J. 23:7-13.

Demick, D.S., Voss, J.L. and Pickett, B.W. 1976. Effect of cooling, storage, glycerization and spermatozoal numbers on equine fertility. J. Anim. Sci. 43:633-637.

DenDaas, J.H.G., De Jong, G., Lansbergen, L.M.T.E. and Van Wagtendonk-De Leeuw, A.M. 1998. The relationship between the number of spermatozoa inseminated and the reproductive efficiency of dairy bulls. J Dairy Sci. 81: 1714-1723.

Donaldson, L. E., AEffect of Insemination Regimen on Embryo Production in Superovulated Cows@, The Veterinary Record, Jul. 13, 1985, pp. 35-37.

Donoghue, A.M., Byers, A.P., Johnston, L.A., Armstrong, D.L. and Wildt, D.E. 1996. Timing of ovulation after gonadotropin induction and its importance to successful intrauterine insemination in the tiger (Panthera tigris). J. Reprod. Fert. 107:53-58.

Douglas, R.H., Nuti, L. and Ginther, O.J. 1974. Induction of ovulation and multiple ovulation on seasonally-anovulatory mares with equine pituitary fractions. Theriogenology. 2(6): 133-142.

Douglas, R.H. 1979. Review of superovulation and embryo transfer in the equine. Theriogenology. 11:33-46.

Duchamp, G., Bour, B., Combamous, Y. and Palmer, E. 1987. Alternative solutions to hCG induction of ovulation in the mare. J. Reprod. Fert. Suppl. 35:221-228.

Evans, M.J. and Irvine, C.H.G. 1977. Induction of follicular development, maturation and ovulation by gonadotropin releasing hormone administration to acyclic mares. Bio. Reprod. 16:452-462.

Fitzgerald, B.P., Peterson, K.D. and Silvia, P.J. 1993. Effect of constant administration of a gonadotropin-releasing hormone agonist on reproductive activity in mares: Preliminary evidence on suppression of ovulation during the breeding season. Am. J. Vet. Res. 54:1746-1751.

Fluharty, F.L., et al., "Effects of Age at Weaning and Diet on Growth of Calves", Ohio Agri. Res. and Dev. Circular, 1996, 156: 29.

Foulkes, J.A., Stewart, D.L. and Herbert, C.N. 1977. Artificial insemination of cattle using varying numbers of spermatozoa. Vet. Rec. 101:205.

Fugger, E.F., AClinical Experience with Flow Cytometric Separation of Human X- and Y- Chromosome Bearing Sperm@, Theriogenology, vol. 52, pp. 1435-1440 (1999).

Fulwyler, M.J. 1977. Hydrodynamic orientation of cells. J Histochem. Cytochem. 25:781-783.

Fulwyler, M.J. 1965. Electronic separation of biological cells by volume. Science. 150:910.

Garner, D.L., Gledhill, B.L., Pinkel, D., Lake, S., Stephenson, D., Van Dilla, M.A. and Johnson, L.A. 1983. Quanti~cation of the X and Y chromosome-bearing spermatozoa of domestic animals by flow cytometry. Biol. Reprod. 28:312-321.

Ginther, O.J. 1992. In: Reproductive Biology of the Mare. (2nd Ed.) Equiservices, Cross Plains, WI.

Ginther, O.J. 1983. Sexual behavior following introduction of a stallion into a group of mares. Theriogenology. 19:877.

Ginther, O.J. 1971. Some factors which alter estrus cycle in mares. J. Anim. Sci. 33:1158. abstr.

Gledhill, B.L. 1988. Gender preselection: historical, technical and ethical perspective. Semin Reprod. Endocrinol. 6:385-395.

Grondahl, C., et al, AIn Vitro Production of Equine Embryos@, Biology of Reproduction, Monograph Series I, pp. 299-307 (1995).

Guillou, F. and Combamous, Y. 1983. Purification of equine gonadotropins and comparative study of their acid-dissociation and receptor-binding specificity. Biochem. Biophys. Acta. 755:229-236.

Gurnsey, M.P., and Johnson, L.A., ARecent improvements in efficiency of flow cytometric sorting of X and Y- chromosome bering sperm of domestic animals: a review@, 1998, New Zealand Society of Animal Protection, three pages.

Harrison, L.A., Squires, E.L. and McKinnon, A.O. 1991. Comparison of hCG, buserelin and luprostiol for induction of ovulation in cycling mares. Eq. Vet. Sci. 3:163-166.

Hofferer, S., Lecompte, F., Magallon, T., Palmer, E. and Combamous, Y. 1993. Induction of ovulation and superovulation in mares using equine LH and FSH separated by hydrophobic interaction chromatography. J. Reprod. Fert. 98:597-602.

Holtan, D.W., Douglas, R.H. and Ginther, O.J. 1977. Estrus, ovulation and conception following synchronization with progesterone, prostaglandin F2 ct and human chorionic gonadotropin in pony mares. J. Anim. Sci. 44:431-437.

Householder, D.D., Pickett, B. W., Voss, J.L. and Olar, T.T. 1981. Effect of extender, number of spermatozoa and hCG on equine fertility. J. Equine Vet. Sci. 1:9-13.

Howard, J.G., Roth, T.L., Byers, A.P., Swanson, W.F. and Wildt, D.E. 1997. Sensitivity to exogenous gonadotropins for ovulation and laparoscopic artificial insemination in the theetab and clouded leopard. Biol. Reprod. 56:1059-1068.

Howard, J.G., Bush, M., Morton, C., Morton, F., Wentzel, K. and Wildt, D.E. 1991. Comparative semen cryopreservation in ferrets (Mustela putorious furo) and pregnancies after laparoscopic intrauterine insemination with frozen-thawed spermatozoa. J. Reprod. Fert. 92:109-118.

Hunter, R.H.F. 1980. Transport and storage of spermatozoa in the female reproductive tract. Proc 4th Int. Congr. Artira. Repro. and A.I. 9:227-233.

Hyland, J.H., Ainsworth, C.G.V. and Langsford, D.A. 1988. Gonadotropin-releasing hormone (GnRH) delivered by continuous infusion induces fertile estrus in mares during seasonal acyclicity. Proc. Amer. Assoc. Eq. Prac. 181-190.

Irvine, C.H.G. and Alexander, S.L. 1993. In: Equine Reproduction. Edited by McKirmon and Voss. Lea and Febiger. Philadelphia, London. pp. 37.

Jasko, D.J., Martin, J.M. and Squires, E.L. 1992. Effect of volume and concentration of spermatozoa on embryo recovery in mares. Theriogenology. 37:1233-1239.

Johnson, A.L. and Becker, S.E. 1988. Use of gonadotropin-releasing hormone (GnRH) treatment to induce multiple ovulations in the anestrous mare. Eq. Vet. Sci. 8:130-134.

Johnson, A.L. 1986. Pulsatile release of gonadotropin releasing hormone advances ovulation in cycling mares. B iol. Reprod. 35:1123☐ 1130.

Johnson, L..A., AAdvances in Gender Preselection in Swine@ Journal of Reproduction and Fertility Supplement, vol. 52, pp. 255-266 (1997).

Johnson, L..A., ASex Preselection in Swine: Altered Sex Ratios in Offspring Following Surgical Insemination of Flow Sorted X- and Y-Bearing Sperm@, Reproduction in Domestic Animals, vol. 26, pp. 309-314 (1991).

Johnson L.A., et al., 1987. Flow cytometry of X- and Y-chromosome bearing sperm for DNA using an improved preparation method and staining with Hoechst 333-42. Garnete Research 17: 203-212.

Johnson, L.A., et al., 1994. Improved flow sorting resolution of X- and Y-chromosome bering viable sperm separation using dual staining and dead cell gating. Cytometry 17 (suppl 7):83.

Johnson, L.A., Flook, J.P., Look, M. V. and Pinkel, D. 1987b. Flow sorting of X and Y chromosome bearing spermatozoa into two populations. Gam. Res. 16:203-212.

Johnson, L.A. 1995. Sex preselection by flow cytometric separation of X and Y chromosome bearing spermatozoa based on DNA difference: a review. Reprod. Fert. Dev. 7:893-903.

Johnson, L.A. 1988. Flow cytometric determination of spermatozoa sex ratio in semen purportedly enriched for X or Y bearing spermatozoa. Theriogenology. 29:265. abstr.

Johnson, L.A. and Schulman, J.D. 1994. The safety of sperm selection by flow cytometry. Ham. Reprod. 9(5):758.

Johnson, L.A., et al, ASex Preselection in Swine: Flow Cytometric Sorting of X- and Y- Chromosome Bearing Sperm to Produce Offspring@, Boar Semen Preservation IV, 2000, pp. 107-114.

Johnson, L.A. and Welch, G.R., ASex Preselection: High-speed flow cytometric sorting of X and Y sperm for maximum efficiency@, Theriogenology, vol. 52, (1999), pp. 1323-1341.

Johnson, L.A., Welch, G.R., Rens, W. and Dobrinsky, J.R. 1998. Enhanced flow cytometric sorting of manunalian X and Y sperm: high speed sorting and orienting No. 77. 1e for artificial insemination. Theriogenology. 49(1):361. abstr.

Johnson, L.A. 1992. Gender preselection in domestic animals using flow cytometrically sorted sperm. J Anim. Sci. Suppl 1.70:8-18.

Johnson, L.A. 1994. Isolation of X- and Y-bearing spermatozoa for sex preselection. In : Oxford Reviews of Reproductive Biology. Ed. HH Charlton. Oxford University Press. 303-326.

Kachel, V., et al., AUniform Lateral Orientation, Cused by Flow Forces, of Flat Particles in Flow-Through Systems@, The Journal of Histochemistry and Cytochemistry, 1997, vol. 25, No. 7, pp. 774-780.

Kanayama, K., Sankai, T., Nariaik, K., Endo, T. and Sakuma, Y. 1992b. Pregnancy by means of tubal insemination and subsequent spontaneous pregnancy in rabbits. J. Int. Med. Res. 20:401-405.

Kilicarslan, M.R., Horoz, H., Senunver, S.C., Konuk, S.C., Tek, C. and Carioglu, B. 1996. Effect of GrnRH and hCG on ovulation and pregnancy in mares. Vet. Rec. 139:119-120.

Lapin, D.R. and Ginther, O.J. 1977. Induction of ovulation and multiple ovulations in seasonally anovulatory and ovulatory mares with an equine pituitary extract. J. Anim. Sci. 44:834-842.

Lawrenz, R. 1985. Preliminary results of non-surgical intrauterine insemination of sheep with thawed frozen semen. J S Afr. Vet Assoc. 56(2):61-63.

Levinson, G., Keyvanfar, K., Wu, J.C., Fugger, E.F., Fields, R.A., Harton, G.L., Palmer, F.T., Sisson, M.E., Starr, K.M., Dennison-Lagos, L., Calvo, L., Sherins, R.J., Bick, D., Schulman, J.D. and Black, S.H. 1995. DNA-based X-enriched sperm separation as an adjunct to preimplantation genetic testing for the preparation of X-linked disease. Mol. Human Reprod. 10:979-982.

Lindsey, A., et al., AHysteroscopic Insemination of Mares with Nonfrozen Low-dose Unsexed or Sex-sorted Spermatozoa@, currently unpublished, pp. 1-15.

Linge, F. 1972. Faltforsok med djupfrost sperma (field trials with frozen sperm). Farskotsel. 52:12-13.

Long, C.R., Rath, D., Welch, G.R., Schreier, L.L., Dobrinsky, J.R., and Johnson, L.A. 1998. AIn vitro production of porcine embryos from semen sorted for sex a with high speed cell sorter: comparison of two fertilization media@, Theriogenology. 49(1):363. abstr.

Loy, R.G. and Hughes, J.P. 1965. The effects of human chorionic gonadotropin on ovulation, length of estrus, and fertility in the mare. Cornell Vet. 56:41-50.

Matsuda, Y. and Tobari, I. 1988. Chromosomal analysis in mouse eggs fertilized in vitro with sperm exposed to ultraviolet light (UV) and methyl and ethyl methanesulfonate (MMS and EMS). Mutat. Res. 198:131-144.

Maxwell, W.M.C., Evans, G., Rhodes, S.L., Hillard, M.A. and Bindon, B.M. 1993. Fertility of Superovulated Ewes after Intrauterine or Oviductal Insemination with Low Numbers of Fresh or Frozen-Thawed Spermatozoa. Reprod. Fertil. Dev. 5:57-63.

McCue, P.M. 1996. Superovulation. Vet. Clin. N. Amer. Eq. Prac. 12:1-11.

McCue, P.M., Fleury, J.J., Denniston, D.J., Graham, J.K. and Squires, E.L. 1997. Oviductal insemination in the mare. 7th Int Symp. Eq. Reprod. 133. abstr.

McDonald, L.E. 1988. Hormones of the pituitary gland. In: Veterinary Pharmacology and Therapeutics. 6th ed. Edited by N.H. Booth and L.E. McDonald. Ames, Iowa State Univ. Press. pp. 590.

McKenna, T., Lenz, R.W., Fenton, S.E. and Ax, R.L. 1990. Nonreturn rates of dairy cattle following uterine body or cornual insemination. J. Dairy Sci. 73:1179-1783.

McKinnon, A. et al, 1993. Predictable ovulation in mares treated with an implant of the GnRH analogue deslorelin. Eq. Vet. J. 25:321-323.

McKinnon, A. and Voss, J., AEquine Reproduction@, Lea & Febiger, Philadelphia, 1993, pp. 291, 299-302, 345-348, 739-797.

McKinnon, A.O. et al, 1996. Repeated use of a GnRH analogue deslorelin (Ovuplant) for hastening ovulation in the transitional mare. Eq. Vet. J. 29:153-155.

Meyers, P.J., Bowman, T., Blodgett, G., Conboy, H.S., Gimenez, T., Reid, M.P., Taylor, B.C., Thayer, J., Jochle, W. and Trigg, T.E. 1997. Use of the GnRH analogue, deslorelin acetate, in a slow release implant to accelerate ovulation in oestrous mares. Vet. Rec. 140:249-252.

Michaels, Charles, ABeef A.I. Facilities that work@, Proc. Fifth N.A.A.B Tech. Conf. A.I. Reprod. Columbia, MO. pp. 20-22.

Michel, T.H., Rossdale, P.D. and Cash, R.S.G. 1986. Efficacy of human chorionic gonadotrophin and gonadatrophin releasing hormone for hastening ovulation in Thoroughbred mares. Eq. Vet. J. 6:438-442.

Miller, S.J. 1986. *Artificial Breeding Techniques in Sheep. In* Morrow, D.A. (ed): Current Therapy in Theriogenology 2. Philadelphia, WB Saunders.

Mirskaja, L.M. and Petrapavlovskii, V.V. 1937. The reproduction of normal duration of heat in the mare by the administration of Prolan. Probl. Zivotn. Anim. Breed. Abstr. 5:387.

Molinia, F.C., Gibson, R.J., Brown, A.M., Glazier, A.M. and Rodger, J.C. 1998. Successful fertilization after superovulation and laparoscopic intrauterine insemination of the brushtail possum, *Trichosurus vulpecula*, and tammar wallaby, *Macropus eugenii*. J.Reprod. Fert. 112:9-17.

Morcom, C.B. and Dukelow, W.R. 1980. A research technique for the oviductal insemination of pigs using laparascopy. Lab. Anim. Sci. 1030-1031.

Morris, L.H., et al., @Hysteroscopic insemination of small numbers of spermatozoa at the uterotubal junction of preovulatory mares@, Journal of Reproduction and Fertility, vol. 118, pp. 95-100 (2000).

Muller, W. and Gautier, F. 1975. Interactions of heteroaromatic compounds with nucleic acids. Euro. J Biochem. 54:358.

Munne, S. 1994. Flow cytometry separation of X and Y spermatozoa could be detrimental to human embryos. Hum. Reprod. 9(5):758.

Pace, M.M. and Sullivan, J.J. 1975. Effect of timing of insemination, numbers of spermatozoa and extender components on pregnancy rates in mares inseminated with frozen stallion semen. J Reprod. Fert. Suppl. 23:115-121.

Peippo, J., et al., ASex diagnosis of equine preimplantation embryos using the polymerase chain reaction@, Theriogenology, vol. 44 619-627 (1995).

Perry, E.J. 1968. Historical Background In: *The Artificial nsemination of Farm Animals*. 4th ed. Edited by E.J. Perry. New Brunswick, Rutgers University Press, pp. 3-12.

Petersen, G.A., et al, "Cow and Calf Performance and Economic Considerations of Early Weaning of Fall-Born Beef Claves", J. Anim. Sci., 1987, 64:15, pp. 15-22.

Pickett, B.W, et al., 1976. Factors influencing the fertility of stallion spermatozoa in an A.I. program. Proc. 8th Internat. Congr. Anim. Reprod. A.I. Krakow, Poland. 4: 1049-1052.

Pickett, B.W., Burwash, L.D., Voss, J.L. and Back, D.G. 1975b. Effect of seminal extenders on equine fertility. J. Anim. Sci. 40:1136-1143.

Pickett, B.W. and Back, D.G. 1973. Procedures for preparation, collection, evaluation and insemination of stallion semen. C.S.U. Exp. Sta. Artira. Reprod. Lab. Gen. Series Bull. 935.

Pickett GW, et al., AManagement of the mare for maximum reproductive efficiency@ Bulletin No. 6 Colorado State University, Ft. Collins Co. (1989).

Pinkel, D., Gledhill, B.L., Van Dilla, M.A., Stephenson, D. and Watchmaker, G. 1982b. High resolution DNA measurements of mammalian spermatozoa. Cytometry. 3:1-9. (1982b).

Rath, D., et al., ALow Dose Insemination Technique in the Pig@, Boar Semen Preservation IV, 2000, pp. 115-118.

Reiling, B.A., et al., "Effect of Prenatal Androgenization on Preformance, Location, and Carcass and Sensory Traits on Heifers in Single Calf Heifer System", J. Anim. Sci., 1995, 73: 986, pp. 986-992.

Rens, W., et al., AA Novel Nozzle for More Efficient Sperm Orientation to Improve Sorting Efficiency of X and Y Chromosome-Bearing Sperm@, Technical Notes, Cytometry 33, 1998, pp. 476-481.

Rens, W., et al., AImproved Flow Cytometric Sorting of X- and Y-Chromosome Bearing Sperm: Substantial Increase in Yield of Sexed Semen@, Molecular Reproduction and Development, 1999, pp. 50-56.

Ritar, A. and Ball, A. 1991. Fertility of young cashmere goats after laparoscopic insemination. J. Agr. Sci. 117:271-273.

Roberts, J.R. 1971. In: *Veterinary Obstetrics and Genital Diseases*. Ithaca, New York. pp. 740-749.

Roser, JF., Evans, J.W., Kiefer, DP., Neeley, D.P. and Pacheco, C.A. 1980. Reproductive efficiency in mares with anti-hCG antibodies. Proc 9th Int. Congr. Artira. Repro. and A.I. 4:627. abstr.

Roth, T.L., Wolfe, B.A., Long, J.A., Howard, J. and Wildt, D.E. 1997. Effects of equine chorionic gonadotropin, human chorionic gonadotropin, and laparoscopic artificial insemination on embryo, endocrine, and luteal characteristics in the domestic cat. Bio Reprod. 57:165-171.

Rowley, H-S., Squires, E.L. and Pickett, B.W. 1990. Effect ofinsemination volume on embryo recover}' in mares. J. Equine Vet. Sci. 10:298-300.

Salamon, S. 1976. *Artificial Insemination of Sheep*. Chippendale, New South Whales. Publicity Press. p. 83-84.

Salisbury, G.W. and VanDemark, N.L. 1961. *Physiology of Reproduction and Artificial Insemination of Cattle*. San Francisco: Freeman and Company.

SAS, SAS/STAT 7 User=s Guide (Release 6.03), SAS Inst. Inc., Cary, NC., 1988. 3 pages.

Schenk, J.L. and Seidel, Jr., G.E., "Imminent Commercialization of Sexed Bovine", Proceedings, The Range Beef Cow Symposium XVL, 1999, pp. 89-96.

Schenk, J.L., ACryopreservation of flow-sorted bovine spermatozoa@, Theriogenology, vol. 52, 1375-1391 (1999).

Schmid R.L., et al, AFertilization with Sexed Equine Spermatozoa Using Intracytoplasmic Sperm Injection and Oviductal Insemination, 7th International Symposium On Equine Reproduction, pp. 139 (Abstract) (1998).

Seidel, G.E. Jr, et al., AInsemination of Heifers with Sexed Sperm A, Theriogenology, vol. 52, pp. 1407-1421 (1999).

Seidel, G.E. Jr, et al., AArtificial Insemination of Heifers with Cooled, Unfrozen Sexed Semen A, Theriogenology, vol. 49 pp. 365 (Abstract) (1998).

Seidel, G.E. Jr., Cran, D.G., Herickoff, L.A., Schenk, J.L., Doyle, S.P. and Green, R.D. 1999. Insemination of heifers with sexed frozen or sexed liquid semen. Theriogenology. 51. (in press). abstr.(1999).

Senger, P.L., Becker, W.C., Davidge, S.T., Hillers, J.K. and Reeves, J.J. 1988. Influence of cornual insemination on conception rates in dairy cattle. J Anim. Sci. 66:3010-3016.

Shelton, J.N. and Moore, N.W. 1967. The response of the ewe tot pregnant mare gonadotropin and to horse anterior pituitary extract. J. Reprod. Fert. 14:175-177.

Shilova, A. V., Platov, E.M. and Lebedev, S.G. 1976. The use of human chorionic gonadothrophin for ovulation date regulation in mares. VIIIth Int. Congr. On Anim. Repro. and A.I. 204-208.

Squires, E.L, Moran, D.M., Farlin, M.E., Jasko, D.J., Keefe, T.J., Meyers, S.A., Figueiredo, E., McCue, P.M. and Jochle, W. 1994. Effect of dose of GnRH analogue on ovulation in mares. Theriogenology. 41:757-769.

Squires, E.L., AEarly Embryonic Loss@ in Equine Diagnostic Ultrasonography, 1st Ed. pp. 157-163 Eds Rantanen & McKinnon. Williams and Wilkins, Baltimore, Maryland (1998).

Squires, E.L.., et al, ACooled and frozen stallion semen@, Bulletin No. 9, Colorado State University, Ft. Collins, CO. (1999).

Sullivan, J.J., Parker, W.G. and Larson, LL. 1973. Duration of estrus and ovulation time in nonlactating mares given human chorionic gonadotropin during three successive estrous periods. J.A.V.M.A. 162:895-898.

Taljaard, T.L., Terblanche, S.J., Berschinger, H.J. and Van Vuuren, L.J. 1991. The effect of the laparoscopic insemination technique on the oestrus cycle of the ewe. J. S Afr. Vet. Assoc. 62(2):60-61.

U.S. Appl. No. 09/511,959 entitled AMethods For Improving Sheath Fluids and Collection Systems For Sex-Specific Cytometer Sorting of Sperm@, filed Feb. 23, 2001.

U.S. Appl. No. 60/211,093, entitled AIntegrated System for Herd Management Using Sexed Semen@, filed Jun. 12, 2000.

U.S. Appl. No. 09/454,488, entitled AImproved Flow Cytometer Nozzle and Flow Cytometer Sample Handling Methods@, filed Dec. 3, 1999.

U.S. Appl. No. 60/224,050, entitled A Integrated System for Herd Management With Terminal-Cross Program Using Sexed Semen@, filed Aug. 9, 2000.

U.S. Appl. No. 60/238,294, entitled AHysteroscopic Insemination of Mares@ filed Oct. 5, 2000.

Vazquez, J., et al., AA.I. in Swine; New Strategy for Deep Insemination with Low Number of Spermatozoa Using a Non-surgical Methodology@, 14th International Congress on Animal Reproduction, vol. 2, Stockhlom, Jul. 2000, p. 289.

Vazquez, J., et al., ASuccessful Low-Dose Insemination by a Fiberoptic Endoscope Technique in the Sow @, Proceedings Annual Conference of the International Embryo Transfer Society, Netherlands, Theriogenology, vol. 53, Jan. 2000, pp. 201.

Vazquez, J., et al.,@Hypoosmotic Swelling Test as Predictor of the Membrane Integrity in Boar Spermatozoa@@, Boar Semen Preservation IV, IVth International Conference on Boar Semen Preservation, Maryland, pp. 263.

Vazquez, J., et al., ADevelopment of a Non-surgical Deep Intra Uterine Insemination Technique@, IV International Conference on Boar Semen Preservation, Maryland, Aug. 1999, p. 35 and photo of display board.

Vidament, M., Dupere, A.M., Julienne, P., Evain, A., Noue, P. and Palmer, E. 1997. Equine frozen semen freezeability and fertility field results. Theriogenology. 48:907.

Voss, J.L., Pickett, B.W., Burwash, L.D. and Daniels, W.H. 1974. Effect of human chorionic gonadotropin on duration of estrous cycle and fertility of normally cycling, nonlactating mares. J.A.V.M.A. 165:704-706.

Voss, J.L., Squires, E.L., Pickett, B.W., Shideler, R.K. and Eikenberry, D.J. 1982. Effect of number and frequency of inseminations on fertility in mares. J. Reprod. Fertil. Suppl. 32:53-57.

Voss, J.L. and Pickett, B.W. 1976. Reproductive management of the broodmare. C.S.U. Exp. Sta. Anim. Reprod. Lab. Gen. Series. Bull. 1-12.

Welch G.R., et al., 1994. Fluidic and optical modifications to a FACS IV for flow sorting of X- and Y- chromosome bearing sperm based on DNA. Cytometry 17 (suppl. 7): 74.

Wilson, C.G., Downie, C.R., Hughes, J.P. and Roser, J.F. 1990. Effects of repeated hCG injections on reproductive efficiency in mares. Eq. Vet. Sci. 4:301-308.

Wilson, M.S. 1993. Non-surgical intrauterine artificial insemination in bitches using frozen semen. J.Reprod. Fert Suppl. 47:307-311.

Woods, J., Bergfelt, D.R. and Ginther, O.J. 1990. Effects of time of insemination relative to ovulation on pregnancy rate and embryonic-loss rate in mares. Eq. Vet. J. 22(6):410-415.

Woods, J. and Ginther, O.J. 1983. Recent studies related to the collection of multiple embryos in mares. Theriogenology. 19:101-108.

Office Action, U.S. Appl. No. 09/001,394, dated Feb. 19, 1999.

Notice of Allowability with Examiner's Amendment, U.S. Appl. No. 09/001,394, dated Oct. 27, 1999.

Office Action, U.S. Appl. No. 09/551,959, dated Jan. 23, 2002.

Notice of Allowability with Examiner's Amendment, U.S. Appl. No. 09/551,959, dated Oct. 15, 2002.

Office Action, U.S. Appl. No. 09/582,809, dated Sep. 17, 2001.

Notice of Allowability with Examiner's Amendment, U.S. Appl. No. 09/582,809, dated Apr. 17, 2002 along with Notice of Withdrawal from Issue dated Oct. 31, 2002.

Office Action, U.S. Appl. No. 09/582,809, dated Oct. 6, 2002.

Office Action, U.S. Appl. No. 09/582,809, dated Oct. 3, 2003.

Office Action, U.S. Appl. No. 09/582,809, dated Jul. 20, 2004.

Office Action, U.S. Appl. No. 09/582,809, dated Apr. 20, 205.

Akhtar, S., et al., "Prevalence of Five Stereotypes of Bluetongue Virus in a Rambouillet Sheep Flock in Pakistan", Veterinary Record 136, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).

Bakker Schut, Tom C. "A New Principle of Cell Sorting by Using Selective Electroportation in a Modified Flow Cytometry," University of Twente, Mar. 10, 1990.

Barnes, F. L. and Eyestone, W. H., "Early Cleavage and the Maternal Zygotic Transition in Bovine Embryos", Therio. vol. 33, No. 1, pp. 141-149. (1990).

Batellier, F. et al., "Advances in Cooled Semen Technology" Animal Reproduction Science 68 p. 181-190 (2001).

Behrman, S. J., et al., "Freeze Preservation of Human Sperm" American Journal of Obstetrics and Gynecology vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Berger, G. S. "Intratubal Insemination", Fertil. Steril. 48:328-330, (1987).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., Et Al., 1999 Sexual Dimorphism In IVM-IVF Bovine Embryos Produced from X and Y Chromosome-Bearing Spermatozoa Sorted By High Speed Flow Cytometry. Theriogenology. 52: 35-48.

BigosBigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Borini et al. Cryopreservation of Mature Oocytes: The use of a trypsin inhibitor enhances fertilization and obtained embryos rates, Fertil. Steril. (1997), vol. 68 (Suppl.).

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef-Production III. Culling Strategies and Nontraditional Management-Systems", J. Anim. Sci. 65:963. 1987.

Branscomb, D. P., The LLNL high-speed sorter: Design features,operational characteristics, and bioloical utility, Cyometry, 6:290-301 (1985).

Braun, J. et al, "Effect of Different Protein Supplements on Motility and Plasma Membrane Integrity of Frozen- Thawed Stallion Spermatozoa", Cryobiology (1995) 32:487-492.

Brink, Z et al. A reliable procedure for superovulating cattle to obtain zygotes and early emryos for microinjection, Theriogenology vol. 41, p. 168, (1994).

Brookes, A. J. and O'Byrne, M., "Use of Cow-Heifers in Beef Production" J. of the Royal Agricultural Society of England 126:30. 1965.

Buchanan, B.R. "Pregnancy Rates in Mares Following a Single Insemination with a Low Number of Spermatozoa into the Tip of the Uterine Horn" Theriogenology p. 395.

Burns, P. D. and Spitzer, J.C., "Influence of Biostimulation on Reproduction in Postpartum Beef-Cows", J. Anim. Sci. 70:358. 1992.

Byerley, D. J., et al., "Pregnancy Rates of Beef Heifers Bred Either on Puberal or Third Estrus". J Anim. Sci. 65:645. 1987.

Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.

Cave-Penney, Tony, "Sexed Semen Offers Faster Genetic Gain", Farming News, Livestock Supplement, Feb. 1997, p. 28.

*Celestron: Telescope Basics*: www.celestron.com/tb-2ref/htm; 4 pages.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Choi, Y.H. "Developmental Cappacity of Equine Oocytes Matured and Cultured in Equine Trophoblast-Conditioned Media" Theriogenoogy 56: 320-339, 2001.

Cran et al. The predetermination of embryonic sex using flow cytometrically separated X and Y spermatozoa, Human Reproduction Update 1996, vol. 2, No. 4 pp. 355-363.

Cran, D.G., et al., "Sex Preselected in Cattle: A Field Trial", Veterinary Record 136, 1995, p. 495-496.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

da Silva, Coutinho M.A.."Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.

Database up 1 BR9704313 (Alves, De Resende et al) Jun. 4, 1999.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

Dhali et al. Vitrification of Buffalo (Bubalus Bubalis)Oocytes, Embryo Theriogenology vol. 53, pp. 1295-1303 (2000).

*Diagnostic Products Corporation,* "Coat-A-Count" http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post- Insemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Doyle, S.P., et al. "Artificial Insemination of Lactating Angus Cows with Sexed Semen". Proc. Western Sect. Am. Soc. Anim. Sci. 50:203. 1999.

Dresser D.W. et at. Analysis of DNAcontent ofLiving Spermatozoa Using Flow Cytometry Technique Journal of Reproduction and Fertility, 1993, vol. 98, pp. 357-365.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Fluorescense Lifetime Systems, www.picoquant.com, Jan. 28, 2005 pp. 2.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Conf. On Artificial Insemination and Reproduction, 62-70 (1984).

Francon, M. and Yamamoto, T., "Un Noveau et tres simple dispositif interferentiel applicable as microscope" Optica Acta 9, p. 395-408.1962.

Fuller, Robert R. "Characterizing Submicron Vesicles With Wavelenth-Resolved Fluorescence in Flow Cytometry," University of Illinois, May 13, 1996.

Gombe, S. and Hansel, W. "Plasma Luteinizing☐Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper-Mayer".

Gottlinger et al., "Operation of a Flow Cytometer", Flow Cytometry and Cell Sorting, A. Radbruch (Ed.), 1992, pp. 7-23.

Graham, J. Analysis of Stallion semen and its Relation to Fertility. abstract.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production.* 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal☐Weaned Calves". I. Prod. Agric. 4:168 (1991).

Hall, J. B., et al., "Effect of Age and Pattern of Gain on Induction of Puberty with a Progestin in Beef Heifers." J. Anim. Sci. 75:1606 (1997).

Hamamatsu Photonics K.K. Electronic Tube Center, Photomultiplier Tubes, Brochure Dec. 1997.

Hamamatsu, *"Photomultiplier Tubes,"* web page, http://www.optics.org/hamamatsu/pmt.html. Printed on Apr. 15, 2000 4.

Hamamatsu, *"Technical Information, Optical Detector Selection: A Delicate Balancing Act"*, web page, http://www.optics.org/hamamatsu/photodiode.html, printed on Apr. 15, 2000, 6 pages total.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harte, F. J. "System of Production of Beef From Once Calved Heifers." In: J.C. Taylor (Ed.) *The Early Calving of Heifers and its Impact on Beef Production.* 123 (1975).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Hermesmeyer, G.N. ,et al. Effects of Lactation and Prenatal Androgenization on the Performance, Carcass Composition, and Longissimus muscle sensory characteristics of heifers in the single-calf heifer system. The Professional Animal Scientist 15: 14-23.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hohenboken, W. D. "Applications of sexed semen in cattle production." Therio. 52:1421. 1999.

Hollinshead F. K. et al. "Production of lambs of predetermined sex after the insemination of ewes with low numbers of frozen-thawed sorted X- or Y- Chromosome-bearing spermatozoa", Reprod. Fertil. And Develop. 2002, vol. 14, pp. 503-508.

Hollinshead F. K. et al. "Sex-Sorting and Re-cryopreservation of Frozen-Thawed Ram Sperm for In Vitro Embryo Production" Theriogenology, vol. 59. (2003) pp. 209.

Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.

Horan, Paul K. "Quantitative Single Cell Ana,lysis and Sorting, Rapid Analysis and sorting of cells is emerging as an important new technology in research and medicine.".

IMV Technologies, Protocol of Bioxcell with Fresh Semen, 1 page, 2000.

IMV Technologies, Protocol of Bioxcell with Frozen Semen, 2 pages, 2000.

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production.* 10. (1975).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, L. A., et al. The Beltsville Sperm Sexing Technology: High-speed sperm sorting gives improved sperm output for In Vitro fertiliation and AI, Journal of Animal Science, vol. 77, Suppl 2/J, Dairy Sci. vol. 82, Suppl. 2/1999 pp. 213-220.

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Successful Gender Preselection in Farm Animals", Agricultural Biotechnology, p. 439-452. 1998).

Joseph, R. L. "Carcass composition and meat quality in once calved heifers." In: J.C. Taylor (Ed.) *The Early Calving of Heifers and its Impact on Beef Production.* 143. (1975).

Joseph, R. L. and J. P. Crowley. "Meat Quality of Once-Calved Heifers." Irish J. of Agric. Research 10:281. (1971).

Keeling, P. "A Modeling Study of Once-Bred Heifer Beef Production." Proceedings of the New Zealand Society of Animal Production. 51. (1991).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle—Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Laster, D. B., "Factors Affecting Dystocia and Effects of Dystocia on Subsequent Reproduction in Beef-Cattle." J. Anim. Sci. 36:695. (1973).

Lightwave Electronics, "Xcyte," www.LightwaveElectronics.com.

Lindsey, A. C., et al., "Low Dose Insemination of Mares Using Non-Sorted and Sex-Sorted Sperm" Animal Reproduction Science 68 p. 279-89 (2001).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Lu, K. H. et al., "In Vitro Fertilization of Bovine Oocytes with Flow-Cytometrically Sorted and Unsorted Sperm from Different Bulls" Therio. abstr.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Manni, Jeff. "To-Photon Excitation Expands the Capabilities of Laser-Scanning Microscopy,".

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) The Early Calving of Heifers and its Impact on Beef Production. (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

McCormick, R. J. "The Flexibility of the Collagen Compartment of Muscle." Meat Sci. 36:79. (1994).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

Meilgaard, M., et al., "Sensor Evaluation Techniques." CRC Press Inc., Boca Raton, FL. (1991).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke,E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/ Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991, vol. 30 pp. 250-257.

Moe, P. W., "Energetics of Body Tissue Mobilization." J. of Dairy Sci. 54:548.

Moran, C., et al., "Puberty in Heifers—a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morgan, J. B., et al., "National Beef Tenderness Survey." J. Anim. Sci. 69: 3274. (1991).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

NCI ETI Branch, Flow CytometryCore Laboratory, http://home.ncifcrf.gov/ccr/flowcore/Isrll.htm, pp. 14, May 11, 2004.

NCI ETI Branch, Flow CytometryCore Laboratory, http://home.ncifcrf.gov/ccr/flowcore/ndyag.htm, pp. 5, May 11, 2004.

Nix, J. P., et al., "Serum Testosterone Concentration, Efficiency of Estrus Detection and Libido Expression in Androgenized Beef Cows." Therio. 49: 1195. (1998).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001 (Su;;l. 1) 64:158.

Olive, M.D., "Detection of Enterotoxigenic Escherichia coli after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Ozhin F.V. et al. Artificial insemination of farm animals. Moscow, Izdatelstvo Selskokhozyaastvennoi Literatury, 1961, pp. 350-361 and pp. 380-393.

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Petit, M. "Early Calving in Suckling Herds." In: J.C. Taylor (ed.) The Early Calving of Heifers and its Impact on Beef Production. p. 157-176. (1975).

Photon, Inc. Light MeasuringSolutions, NanoScan for High-powered beam Applications, 2005.

Picket B.W., et al., "Livestock Production Science," 1998.

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "The Effect of Extenders, Spermatozoal Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds.), 1985, pp. 77-128.

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Prokofiev M.I. Regoulyatsia Razmnozhenia Selskokhozyastvennykh Zhivotnykh, Leningrad, NAOUKA Publishing House, 1983, pp. 181-195.

Province, C.A., et al., Cooling Rates, Storage, Temperatures and Fertility of Extended Equine Spermatozoa Therio. vol. 23 (6) p. 925-934, Jun. 1985.

Pursel, et al, "Effect of Orvus ES Paste on Acrosome Morphology, Motility and Fertilizing Capacity of Frozen-Thawed Boar Sperm," Journal of Animal Science, 47:1:198-202 (1978).

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rathi, R. et al., "Evaluation of In Vitro Capacitation of Stallion Spermatoza", Biology of Reproduction 2001, vol. 65, pp. 462-470.

Recktenwald, Diether. "Cell Separation Methods and Applications," New York 1997.

Reiling, B.A., et al., "Effects of Prenatal Androgenization and Lactation on Adipose Tissue Metabolism in Finishing Single-Calf Heifers" J. Anim. Sci. vol. 75 p. 1504-1512 (1997).

Reiling, B.A., et al., "Effects of prenatal Androgenization, Melegestrol Acetate, and Synovex-H on Feedlot Performance, Carcass, and Sensory Traits of Once-Calved Heifers" J. Anim. Sci. vol. 74 p. 2043-51 (199).

Rens W., et al Slit-scan flow cytometry for consistent high resdolution DNA analysis of X- and Y- chromosome bearing sperm, Cytometry 25:191-199 (1996).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysterscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production*. 23. (1975).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Roy, J. H., "Rearing Dairy-Herd Replacements." Journal of the Society Of Dairy Technology 31:73-79 (1978).

Rutter, L. M., et al., "Effect of Abomasal Infusion of Propionate on the GnRH-Induced Luteinizing Hormone Release in Prepuberal Heifers." J. Anim. Sci. 56:1167 (1983).

Schenk, J. L. "Applying Semen Sexing Technology to the AI Industry", Proceedings of the 18th Technical Conference on Artificial insemination & Reproduction, 2000.

Schillo, K. K., et al, "Effects of Nutrition and Season on the Onset of Puberty in the Beef Heifer." J. Anim. Sci. 70:3994 (1992).

Schnell, T. D., et al, "Performance, Carcass, and Palatability Traits for Cull Cows Fed High-Energy Concentrate Diets for 0, 14, 28, 42, or 56 days." J. Anim. Sci. 75:1195 (1997).

Schoonmaker, J. P., et al., "Effects of Age at Weaning and Implant Strategy on Growth of Steer Calves." J. Anim. Sci. (Suppl. II) 76:71. (1998) abstr.

Scmid, R. L., et al. Effects of follicular fluid or progesterone on *in vitro* maturation of equine oocytes before intracytoplasmic sperm injection with non-sorted and sex-sorted spermatozoa, Journal of Reproduction and Fertility 56:519-525, 2000.

Seidel, G. E. Jr et al., "Current Status of Sexing Mammalian Spermatozoa," Society for Reproduction and fertiity, pp. 733-743, 2002.

Seidel, G. E. Jr. "Cryopreservation of Equine Embryos" Veterinary Cliniics of North America: Equine Practice vol. 12, No. 1, Apr. 1996.

Seidel, G. E. Jr. "Sexing Bovine Sperm" The AABP Proceedings—vol. 34.

Seidel, G. E. Jr. Sexing mammalian spermatozoa and embryos—state of the art Journal of Reproduction and Fertility Supp 54, 477-487 1999.

Seidel, G. E. Jr., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G. E. Jr., "Commercilizing Repreductive Biotechnology—The Approach used by XY, Inc.," Theriogenology, p. 5, 1999.

Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.

Seidel, G. E. Jr., "Status of Sexing Semen for Beef Cattle", Texas A & M University 45th Annual Beef Cattle Short Course and Trade Show Proceedings, Aug. 9-11, p. III24-III27, (1999).

Seidel, G. E. Jr., Economics of Selecting for Sex: The Most Important Genetic Trait, Theriogenology 59, (2003), pp. 585-598.

Seidel, G. E. Jr., et al, "Sexing Mammalian Sperm—Overview", Therio. 52: 1267-1272, (1999).

Seidel, G. E. Jr., et al., "Insemination of Heifers with Sexed Frozen or Sexed Liquid Semen." Therio. 51. (in press) (1999) abstr.

Sell, R. S., et al., "Single-calf Heifer Profitability Compared to Other North Dakota Beef Production Systems." Department of Ag. Eco., North Dakota State University, Ag. Econ. Rpt. 20.

Shabpareh, V. "Methods for Collecting and Maturing Equine Oocytes in Vitro" Theriogenology 40: 1161-1175, 1993.

Shackelford, S. D., et al, "Effects of Slaughter Age on Meat Tenderness and USDA Carcass Maturity Scores of Beef Females." J. Anim. Sci. 73:3304. (1995).

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997. Abstract.

Sharpe, Johnathan, Thesis; "An Introduction of Flow Cytometry", Ch. 2-2.2, 1997.

Sharpe, Johnathan, Thesis; "Gender Preselection—Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine.

Solsberry G.U., Van-Denmark N.L., Theory and practice of artificial cow insemination in USA, Moscow, KOLOS Publishing House, 1966, p. 346.

Spectra Physics, The Solid State Laser Company, "Vangaurd 4 Watts of UV from a Quasi-CW, All Solid State Laser," http://www.splasers.com/products/isl_products/vangaurd.html three pages, printed Nov. 14, 2002.

Spectra-Physics Products, "Fcbar" http://www.splasers.com/products/oem_products/ov_fcbar.html two pages printed Nov. 14, 2002.

Spectra-Physics, The Solid State Laser Company, Vanguard 2000-HMD 532, www.specra-physics.com.

Spectra-Physics, The Solid State Laser Company, Vanguard 350-HMD 355, User's Manual, Dec. 2002.

Spectra-Physics, The Solid State Laser Company, Vanguard 350-HMD 355, www.specra-physics.com.

Squires, E.L., "Procedures for Handling Frozen Equine Semen for Maximum Reproductive Efficiency", pp. 1, 39-41, 81-89.

Staigmiller, R.B. "Superovulation of Cattle with Equine Pituitary Extract and Porcine FSH" Theriogenology 37: 1091-1099 1992.

Stap J. Et al Improving the Resolution of Cryopreserved X- and Y- Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments abstract only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sumner, A. T. and Robinson, J. A., "A Difference in Dry Mass Between the Heads of X and Y- Bearing Human Spermatozoa", J Reprod Fertil. 48, p. 9-15 (1976).

Swanson, E. W. "Future Research on Problems of Increasing Meat Production by Early Calving." In: J.C. Taylor (ed.) *The Early Calving of Heifers and its Impact on Beef Production.* (1975).

Tatum, J. D., et al., "Carcass Characteristics, Time on Feed and Cooked Beef Palatability Attributes." J. Anim. Sci. 50:833. (1980).

Taylor, C. S., "Efficiency of Food Utilization in Traditional and Sex-Controlled Systems of Beef Production", AFRC Animal Breeding Research Organization, West Mains Road, Edinburg EH9 3JQ, pp. 401-440.

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS—Egg Yolk Extender for Cryopreservation of Bull Semen; Theriogenology Symposium, December 1999, vol. 52, #8.

*Time-Bandwidth Products "GE—100—XHP",* www.tbsp.com, 2 pages, Jan. 2002.

Unruh, J. A. "Effects of Endogenous and Exogenous Growth-Promoting Compounds on Carcass Composition, Meat Quality and Meat Nuritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

Van Munster, E. B., "Geslachtsbepaling met interferometrie", Derde prijs NtvN-prijsvraag voor pas-gepromoveerden 65/4, (Sex Determination with Interferometry) p. 95-98 (1999).

Van Munster, E. B., et al, "Difference in Sperm Head Volume as a Theoretical Basis for Sorting X & Y-Bearing Spermatozoa: Potentials and Limitations", Therio 52, pp. 1281-1293 (1999).

Van Munster, E. B., et al, "Difference in Volume of X- and Y-chromosome Bearing Bovine Sperm Heads Matches Difference in DNA Content" Cytometry vol. 35 p. 125-128 (1999).

Van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

Van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

van Munster, E. B. Interferometry in flor to sort unstained X- and Y-Chromosome-Bearing Bull Spermatozoa, Cytometry 47:192-199 (2002).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Waggoner, A. W., et al., "Performance, Carcass, Cartilage Calcium, Sensory and Collagen Traits of Longissimus Muscles of Open Versus 30-month-old Heifers That Produced One Calf." J. Anim. Sci. 68:2380. 1990.

Watson, "Recent Developments and Concepts in the Cryopreservation of Spermatozoa and the Assessment of Their Post-Thawing Function," Reprod. Fertil. Dev. 7:871-891 (1995) ABSTRACT.

Wheeler, T. L., et al., "Effect of Marbling Degree on Beef Palatability in Bos-taurus and Bos-indicus cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilhelm, K.M. et al, "Effects of Phosphatidylserine and Cholesterol Liposomes on the Viability, Motility, and Acrosomal Integrity of Stallion Spermatozoa Prior to and after Cryopreservation", Cryobiology 33:320, 1996.

Wilson, D. E. et al., "Mammal Species of the World", Smithsonian Institution Press, 1993, 1206 pp.

Windsor, D. P., et al, "Sex Predetermination by Separation of X and Y Chromosome-bearing Sperm: A Review", Reproduction of Fertilization and Development 5, pp. 155-171, (1993).

Wintzer Et al.:"Krankheiten des Pferdes Ein Leitfaden fur Studium und Praxiz," 1982, nParey, Berlin Hamburg XP002281450.

Zhou, Hongwei, et al. "Research on and Development of Flow Cell Sorting Apparatuses," Gazette of Biophysics, vol. 13, ed. 3, 1997.

U.S. Appl. No. 09/015,454, Office Action dated Sep. 14, 1998 (SuperO-Orig U.S. nonprovisional).

U.S. Appl. No. 09/015,454, Office Action dated May 24, 1999 (SuperO-Orig U.S. nonprovisional.

U.S. Appl. No. 09/015,454, Notice of Allowability with Examiner's Amendment, dated Dec. 27, 1999) (SuperO-Orig).

U.S. Appl. No. 09/448,643, Office Action dated Mar. 21, 2001 (SuperO-Cont1).

U.S. Appl. No. 09/448,643, Office Action dated Jun. 1, 2000 (SuperO-Cont1).

U.S. Appl. No. 09/448,643, Notice of Allowability with Examiner's Amendment dated Oct. 9, 2001 (SuperO-Cont1).

U.S. Appl. No. 10/081,955, Office Action dated Sep. 30, 2004 (SuperO-Cont2).

U.S. Appl. No. 10/081,955, Office Action dated Jun. 13, 2005 (SuperO-Cont2).

Australian application No. 20239/99; Examiner'Report dated Oct. 3, 2001 (Parent).

Australian application No. 20239/99; Examiner's Report dated Nov. 14, 2001 (Parent).

Australian application No. 20239/99; Examiner's Report dated Apr. 2, 2003 (Parent).

Australian application No. 20239/99; Examiner's Report dated May 13, 2003 (Parent).

Australian application No. 20239/99; Letters Patent dated Mar. 18, 2004.

Australian application No. 2003213537; Examiner's Report dated May 23, 2005 (Div1).

Canadian Application No. 2,316,080; Examiner's Report dated Jul. 14, 2003.

Canadian Application No. 2,316,080; Examiner's Report dated Mar. 31, 2005.

Chinese Application No. 98813255.9; Office Action dated Oct. 10, 2003.

European Regional Application No. 98 965 046.0; dated Feb. 23, 2004.

European Regional Application No. 98 965 046.0; dated Nov. 15, 2004.

European Regional Application No. 98 965 046.0; dated Jun. 27, 2005.

Great Britain application No. GB-0016132.3; Examination Report dated Apr. 9, 2002 (Parent).

Great Britain application No. GB-0016132.3; Examination Report dated Nov. 1, 2002 (Parent).

Great Britain application No. GB-0016132.3; Examination Report dated Feb. 10, 2003 (Parent).
Great Britain application No. GB-0016132.3; Examination Report dated Mar. 25, 2003 (Parent).
Great Britain application No. GB-0016132.3; Examination Report dated Apr. 9, 2003 (Parent).
Great Britain application No. GB-0016132.3; Certificate of Grant of Patent No. GB 2350619 dated Jun. 4, 2003 (Parent).
Great Britain application No. GB-0300479.3; Combined Search and Examination Report dated Feb. 13, 2003 (Div1).
Great Britain application No. GB-0300479.3; Examination Report dated Mar. 28, 2003 (Div1).
Great Britain application No. GB-0300479.3; Examination Report dated Apr. 10, 2003 (Div1).
Great Britain application No. GB-0300479.3; Certificate of Grant of Patent No. GB2381005 dated Jun. 4, 2004 (Div1).
Great Britain application No. GB-0300478.5; Combined Search and Examination Report dated Feb. 13, 2003 (Div2).
Great Britain application No. GB-0300478.5; Examination Report dated Mar. 26, 2003 (Div2).
Great Britain application No. GB-0300478.5; Certificate of Grant of Patent No. GB2381004 dated Jun. 4, 2004 (Div2).
Great Britain application No. GB-0300480.1; Combined Search and Examination Report dated Feb. 13, 2003 (Div3).
Great Britain application No. GB-0300480.1; Examination Report dated Apr. 2, 2003 (Div3).
Great Britain application No. GB-0300480.1; Examination Report dated Apr. 17, 2003 (Div3).
Great Britain application No. GB-0300480.1; Certificate of Grant of Patent No. GB2381006 (Div3).
German Application No. 198 82 943.4-41; Office Action dated Apr. 26, 2002.
Japanese Application No. 2000-526614; Notice of Reasons for Rejection dated May 27, 2004.
New Zealand Application No. 505330; Examination Report dated May 16, 2001 (Parent).
New Zealand Application No. 505330; Examination Report dated Nov. 25, 2002 (Parent).
New Zealand Application No. 505330; Grant of Patent dated Jun. 9, 2003 (Parent).
New Zealand Application No. 522607; Examination Report dated Nov. 21 2002 (Div1).
New Zealand Application No. 522607; Examination Report dated Mar. 8, 2004 (Div1).
New Zealand Application No. 522607; Examination Report dated May 19, 2004 (Div1).
New Zealand Application No. 522607; Grant of Patent dated Dec. 9, 2004 (Div1).
New Zealand Application No. 532939; Examination Report dated May 19, 2004 (Div2).
Russian Application No. 2000120216/13; Official Action dated Jan. 28, 2003.
Russian Application No. 2000120216/13; Official Action dated Oct. 27, 2003.
Russian Application No. 2000120216/13; Official Action dated May 25, 2005.
Saacke,R.G., Can Spermatozoa with abnormal heads gain access to the ovum in artificially inseminated super- and single-ovulating cattle?, Theriogenology 50:117-128. 1998.
Hawk, H.W., Gamete Transport in the Superovulated Cow. Theriogenology: Jan. 1998 vol. 29 No. 1 pp. 125-142.
Blecher, S.R., et al. A new approach to immunological sexing of sperm, Theriogenology, 59, pp. 1309-1321, 1999 vol.
Wheeler, M. B., et al. Application of sexed semen technology to in vitro embryo production in cattle, Theriogenology, vol. 65 (2006) 219-227.
Garverick, H. A., et al. mRNA and protein expression of P450 aromatase (AROM) and estrigen receptors (ER) $\alpha$ and $\beta$ during early development of bovine fetal ovaries; The society for the study of reproduction 38th annual meeting Jul. 24-27, 2005; Abstract only.
Bodmer, M., et al., Fertility in heifers and cows after low does insemination with sex-sorted and non-sorted sperm under field conditions; Theriogenology, vol. 64, (2005) 1647-1655.
Schenk J. L., et al. Embryo production from superovulated cattle following insemination of sexed sperm, Theriogenology, 65 (2006) 299-307.
Garner, D. L., Flow cytometric sexing of mammalian sperm, Theriogenology, (2006) pp. 15.
Habermann F. A., et al., Validation of sperm sexing in the cattle (Bos taurus) by dual colour flourescence in situ hybridization; J Anim Breed Genet. Apr. 2005; 122 Suppl 1:22-7 (Abstract only).
U.S. Appl. No. 09/582,809, Office Action dated May 1, 2006).
U.S. Appl. No. 10/081,955, Office Action dated Mar. 14, 2006l.
Johnson, L. A., Sexing mammalian sperm for production of offspring: the state-of-the-art; Animal Reproduction Science; 60-61 (2000) pp. 93-107.
Seidel, G.E. Jr., et al., Methods of Ovum Recovery and Factors Affecting Fertilization of Superovulated Bovine Ova, Control of Reproduction in the Cow, Sneenan ed., 1978, pp. 266-280.
Hawk, H. W. et al., Effect-of Unilateral Cornual Insemination upon Fertilization Rate in Superovulating and Single-Ovulating Cattle, Journal of Animal Sciences, 1986 vol. 63, pp. 551-560.
Andersson, M. et al., Pregnancy Rates in Lactating Holstein-Greisian Cows after Artificial Insemination with Sexed Sperm. Reprod. Dom. Anim 41, 95-97, 2006.
Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.
Wilson, R. D., et al., In vitro production of bovine embryos using sex-sorted sperm, Theriogenology, 65 (2006) 1007-1015.

* cited by examiner

COLLECTION SYSTEMS FOR CYTOMETER SORTING OF SPERM

This application is a division of U.S. application Ser. No. 09/511,959, filed on Feb. 23, 2000 and now issued as U.S. Pat. No. 6,524,860, which is a division of U.S. patent application Ser. No. 09/001,394, filed on Dec. 31, 1997 and now issued as U.S. Pat. No. 6,149,867.

I. BACKGROUND OF THE INVENTION

This invention relates generally to the field of sex selection in mammalian offspring. It is especially relevant to the aspect of low dose artificial insemination for creating the desired sex of offspring. Particularly, the invention relates to systems for sorting sperm via flow cytometry for sex-specific and low dose efforts at artificial insemination or the like.

For ages it has been desired to select the sex of specific offspring. Beyond obvious psychological aspects, the actual sex selection of mammalian offspring has significant economic consequences when one considers its application to food producing animals such as cattle as well as celebrated trophy animals such as horses and the like. This great desire has resulted in a significant variety of efforts to achieve sex-selected offspring. Probably the effort which has appeared most likely to achieve the desired results has been efforts at sorting and selecting between X and Y sperm prior to insemination.

One of the challenges that effort at sorting X and Y sperm has faced is the large numbers of sperm involved. In natural insemination sperm are produced in some species by the billions; in artificial insemination less, but still significantly large numbers of sperm are used. For instance, artificial insemination techniques commonly use ten million to five hundred million sperm (depending on species). Thus a significant number of sperm are necessary even in an artificial insemination environment.

Many methods have been attempted to achieve the separation of X- and Y-chromosome bearing sperm. These methods have ranged from magnetic techniques such as appears disclosed in U.S. Pat. No. 4,276,139 to columnar techniques as appears disclosed in U.S. Pat. No. 5,514,537 to gravimetric techniques as discussed in U.S. Pat. No. 3,894,529, reissue Pat. No. 32350, U.S. Pat. Nos. 4,092,229, 4,067,965, and 4,155,831. Electrical properties have also been attempted as shown in U.S. Pat. No. 4,083,957 as well as a combination of electrical and gravimetric properties as discussed in U.S. Pat. Nos. 4,225,405, 4,698,142, and 4,749,458. Motility efforts have also been attempted as shown in U.S. Pat. Nos. 4,009,260 and 4,339,434. Chemical techniques such as those shown in U.S. Pat. Nos. 4,511,661 and 4,999,283 (involving monoclonal antibodies) and U.S. Pat. Nos. 5,021,244, 5,346,990, 5,439,362, and 5,660,997 (involving membrane proteins), and U.S. Pat. Nos. 3,687,803, 4,191,749, 4,448,767, and 4,680,258 (involving antibodies) as well as the addition of serum components as shown in U.S. Pat. No. 4,085,205. While each of these techniques has been presented as if to be highly efficient, in fact at present none of those techniques yield the desired level of sex preselection.

At present, the only quantitative technique used to achieve the separation of X-and Y-chromosome bearing sperm has been that involving individual discrimination and separation of the sperm through the techniques of flow cytometry. This technique appeared possible as a result of advances and discoveries involving the differential dye absorption of X-and Y-chromosome bearing sperm. This was discussed early in U.S. Pat. No. 4,362,246 and significantly expanded upon through the techniques disclosed by Lawrence Johnson in U.S. Pat. No. 5,135,759. The Johnson technique of utilizing flow cytometry to separate X- and Y-chromosome bearing sperm has been so significant an advancement that it has for the first time made the commercial separation of such sperm feasible. While still experimental, separation has been significantly enhanced through the utilization of high speed flow cytometers such as the MoFlo® flow cytometer produced by Cytomation, Inc. and discussed in a variety of other patents including U.S. Pat. Nos. 5,150,313, 5,602,039, 5,602,349, and 5,643,796 as well as international PCT patent publication WO 96/12171. While the utilization of Cytomation's MoFlo® cytometers has permitted great increases in speed, and while these speed increases are particularly relevant given the high number of sperm often used, certain problems have still remained. In spite of the almost ten-fold advances in speed possible by the MoFlo® flow cytometer, shorter and shorter sorting times have been desired for several reasons. First, it has been discovered that as a practical matter, the sperm are time-critical cells. They loose their effectiveness the longer they remain unused. Second, the collection, sorting, and insemination timings has made speed an item of high commercial importance. Thus, the time critical nature of the sperm cells and the process has made speed an essential element in achieving high efficacy and success rates.

Other problems also exist ranging from the practical to the theoretical. On the practical side, it has been desired to achieve sex-sorted sperm samples using inexpensive disposable components and substances. Also on the expense side, it has been desired to be able to achieve sorting (as well as collection and insemination) in as efficient a labor event as possible. Thus, for commercial production and success in this field, improvements which might only represent an increase in efficiency may still be significant. Related to the practical aspect of expense, is the practical aspect of the delicateness and sensitivity of the entire process. In this regard, it has been desired to simplify the process and make it as procedurally robust as possible so that operator error or skill can play an ever decreasing role.

In addition to the delicateness of the process, it has always been known that the sperm themselves are extremely delicate cells. While this factor at first glance seems like it might be considered easily understood, in fact, the full extent of the cells' sensitivities have not yet been fully explored. In the context of flow cytometry in general, most sorted cells or particles have often been spherical or otherwise physically able to withstand a variety of abuses. This is not the case for sperm cells. In fact, as the present invention discloses, the processing through normal flow cytometer techniques may, in fact, be unacceptable for cytometric sorting of sperm cells in certain applications. The sensitivities range from dilution problems and the flow cytometer's inherent need to isolate and distinguish each cell individually as well as the pressure and other stresses which typical flow cytometry has, prior to the present invention, imposed upon the cells or other substances that it was sorting. This may also represent a unique factor for sperm cells because it appears that even though the sperm cell may appear to pass through the flow cytometer and be sorted with no visually discernable side-effects, in fact, the cells themselves may have been stressed to the point that they perform less than optimally in the insemination process. Thus, an interplay of factors seems involved and has raised unusual problems from the perspective of sperm cell sorting and ultimate use for artificial insemination.

Another problem which has remained—in spite of the great advances achieved through the Johnson patent and related technology—is the fact that prior to the present invention it has been extremely difficult to achieve lower dosage insemination with sexed sperm. While historically, some achievement of low dose insemination has occurred, it has appeared to be more on a theoretical or laboratory environment rather than from environments which are likely to be experienced in or applicable to a commercial application. In this regard, the desire has not been merely to achieve low dose insemination but rather to achieve low dose insemination with pregnancy success rates which are comparable to existing unsexed, high dosage artificial insemination efforts. Thus, the advances achieved by the present inventors in both sexed and low dose artificial insemination represent significant advances which may, for the first time, make commercial applications feasible.

Another problem which has been faced by those in the industry—again, in spite of the great advances by the Johnson patent and related technology—is the fact that the problem itself, namely, artificial insemination with a high success rate is one of a statistical nature in which a multitude of factors seem to interplay. Thus, the solutions proposed may to some degree involve a combination of factors which, when thoroughly statistically studied, will be shown to be necessary either in isolation or in combination with other factors. Such a determination is further compounded by the fact that the results themselves vary by species and may be difficult to ascertain due to the fact that testing and statistical sampling on a large enough data base is not likely to be worth the effort at the initial stages. For these reasons the invention can also involve a combination of factors which may, individually or in combination, represent the appropriate solutions for a given application. This disclosure is thus to be considered broad enough so that the various combinations and permeations of the techniques disclosed may be achieved. Undiscovered synergies may exist with other factors. Such factors may range from factors within the sorting or flow cytometer steps to those in the collection as well as insemination steps. At present, studies have been primarily achieved on bovine species, however, it is not believed that these techniques will be limited to such species or, for that matter to only sperm cells. It appears that the techniques used may have application beyond just sperm cells into areas which involve either sensitive items to be sorted or merely minimization of the impacts of the stresses of flow cytometry upon the item sorted.

Interestingly, while the present invention takes an approach to minimize the impacts and stresses upon the sperm cells, others appear to have actually taken steps away from this direction by increasing pressures and demands for speed and other such performance. Essentially, the drive for low dose insemination and high speed processing may, in an individual or perhaps interrelated fashion have posed problems which limited one another. Thus, while there has been a long felt but unsatisfied need for high speed, low dose sexed insemination, and while the implementing arts and elements have long been available, prior to the present invention the advances or perhaps combinations of advances had apparently been overlooked by those skilled in the art. Perhaps to some degree they failed to appreciate that the problem involved an interplay of factors as well as peculiar necessities for the types of cells (sperm cells or perhaps species-specific sperm cells) involved in this field. Interestingly, as the listing of efforts earlier in this discussion shows, substantial attempts had been made but they apparently failed to understand the problem inherent in such an area as low dose, sexed insemination and had perhaps assumed that because the natural service event involves perhaps billions of sperm, there may have been physical limitations to the achievement of artificial insemination with numbers which are as many as four orders of magnitude less in number. Thus, it may not be surprising that there was to some extent an actual teaching away from the technical direction in which the present inventors went. Perhaps the results may even be considered unexpected to a degree because they have shown that sexed, low dose artificial insemination can be achieved with success rates comparable to those of unsexed, high dose artificial insemination. It might even be surprising to some that the techniques and advances of the present invention in fact combine to achieve the great results shown. While each technique could, in isolation, be viewed by some as unremarkable, in fact, the subtle changes appear to afford significant advances in the end result—whether considered alone or in combination with other subtle changes.

Thus, until the present invention the achievement of success rates for low dose, sexed artificial insemination has not been possible with levels of performance necessary or simplified procedures likely to be necessary to achieve commercial implementation. The present invention discloses techniques which permit the achievement of improved performances and thus facilitate the end result desired, namely, low dose, sexed artificial insemination on a commercial basis.

II. SUMMARY OF THE INVENTION

Accordingly, the present invention provides improved sheath and collector systems for sorting of sperm cells to determine their sex through a flow cytometer. The sheath fluid as typically used in a flow cytometer is replaced with a fluid which minimizes the stress on the sperm cells as they are sorted. Furthermore, the collection system is improved to minimize both the physical and chemical stress to which the sperm cells are subjected. Various techniques and substances are represented but as those skilled in the art will readily understand, various combinations and permutations can be used in the manner which may be optimized for performance based in the species, goals and other parameters involved in a specific processing application.

An object of the invention is thus to achieve better sorting for substances such as sperm cells. A goal is to minimize the impact the sorting function itself has on the cells or other sensitive items which may be sorted. A particular goal is to minimize the impact the sheath fluid imposes upon the cells and to potentially provide a sheath fluid which affirmatively acts to assist the cells in handling the various stresses involved. A parallel goal is to provide substances and techniques which are especially suited for sperm cells in general, for bovine sperm cells, for equine sperm cells, and for the separation of such sperm cells into X- and Y-chromosome bearing components. Similarly a goal is to minimize the impacts that the collection phase (e.g., after sorting) has upon the cells and to minimize the physical impact as well as chemical impacts on such sex sorted sperm cells. Thus a goal is to achieve as unaffected a sorted result as possible.

Another object of the invention is to achieve low dose, sorted insemination on levels and with success rates which are comparable to those of the typical unsexed, high dose artificial insemination. Thus the prior goals of minimizing the stress or potential damage upon the sperm cells is important. Sorting in a manner which affords both high speed and low stress sorting, and which is especially adapted for sperm cell sorting in a low dose context is an important goal as well. The goals of providing sheath and other fluids which do not negatively affect the fertility of the sperm and which are compatible with artificial insemination are also important.

Naturally further objects of the invention are disclosed throughout other areas of the specification and claims.

III. BRIEF DESCRIPTION OF DRAWINGS

FIG. 1 is a schematic diagram of a sorter system according to the present invention.

FIG. number 2 is a diagram of the entrained cells in the free fall area of a typical flow cytometer.

Figure 3:
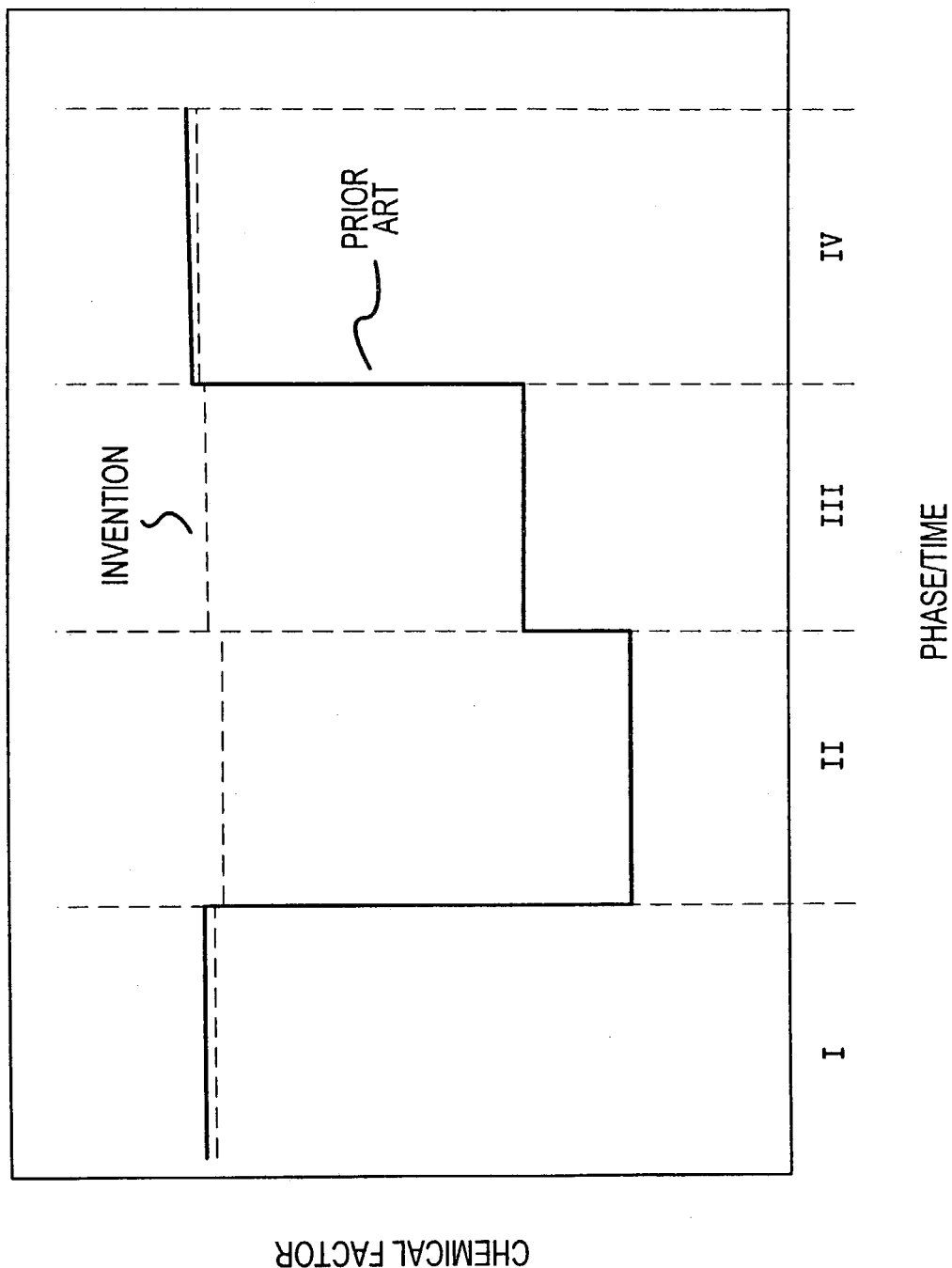

FIG. 3 is a conceptual diagram showing differences as they roughly appear as a result of the present invention.

FIG. number 4 is a diagram of the sorted cell stream as they are collected in the landing zone area.

IV. DETAILED DESCRIPTION OF THE PREFERRED EMBODIMENT

As will be seen, the basic concepts of the present invention can be combined and embodied in a variety of ways. The invention involves both improved flow cytometer systems as well as systems for the creation of sex-specific sperm samples which may be used in artificial insemination and the animals produced by such techniques. Furthermore, the techniques are disclosed in a general fashion so that they may be applied to specific systems and applications once the general principals are understood. While device enhancements are disclosed it should be understood that these enhancements not only accomplish certain methods but also can be varied and combined in a number of ways. Importantly, as to all of the foregoing, each of these facets should be understood to be encompassed by this disclosure.

As mentioned, the basic goal is that of separating the X-bearing sperm from the Y-bearing sperm. This is done in a manner which isolates the two types of sperm so that each can be separately packaged and dealt with. The isolation is preferably done through the use of flow cytometry. Flow cytometry in general is a technique which is well understood. For instance, the basic aspects of it are shown and discussed in a variety of patents to Cytomation, Inc. such as the U.S. patents and other publications listed earlier. Each of these patents and the references cited therein, are incorporated by reference, thus those skilled in the art can easily understand the basic principles involved.

Essentially, flow cytometry involves sorting items, such as cells, which are provided to the flow cytometer instrument through some type of cell source. A conceptual instrument is shown in FIG. 1. The flow cytometer instrument includes a cell source (1) which acts to establish or supply cells or some other type of item to be analyzed by the flow cytometer. The cells are deposited within a nozzle (2) in a manner such that the cells are surrounded by a sheath fluid (3). The sheath fluid (3) is usually supplied by some sheath fluid source (4) so that as the cell source (1) supplies its cells, the sheath fluid (3) is concurrently fed through the nozzle (2). In this manner it can be easily understood how the sheath fluid (3) forms a sheath fluid environment for the cells. Since the various fluids are provided to the flow cytometer at some pressure, they flow out of nozzle (2) and exit at the nozzle orifice (5).

By providing some type of oscillator (6) which may be very precisely controlled through an oscillator control (19), pressure waves may be established within the nozzle (2) and transmitted to the fluids exiting the nozzle (2) at nozzle orifice (5). Since the oscillator (6) thus acts upon the sheath fluid (3), the stream (7) exiting the nozzle orifice (5) eventually and regularly forms drops (8). Because the cells are surrounded by a sheath fluid environment, the drops (8) may contain within them individually isolated (generally) cells or other items.

Since the drops (8) generally contain isolated cells, the flow cytometer can distinguish and separate droplets based upon whether or not the appropriate cell or cells is/are contained within the drop. This is accomplished through a cell sensing system (9). The cell sensing system involves at least some type of sensor (10) which responds to the cells contained within each drop (8) as discussed at length in the seminal work (no pun intended) by Larry Johnson, namely, U.S. Pat. No. 5,135,759. As the Johnson patent explains for sperm cells, the cell sensing system (9) may cause an action depending upon the relative presence or relative absence of a particular dye which may be excited by some stimulant such as the laser exciter (11). While each type of sperm cell is stained by the dye, the differing length of the X-chromosome and the Y-chromosome causes different levels of staining, Thus, by sensing the degree of dye present in the sperm cells it is possible to discriminate between X-bearing sperm and Y-bearing sperm by their differing emission levels.

In order to achieve the ultimate separation and isolation of the appropriate cells, the signals received by sensor (10) are fed to some type of sorter discrimination system (12) which very rapidly makes the decision and can differentially charge each drop (8) based upon whether it has decided that the desired cell does or does not exist within that drop (8). In this manner the sorter discrimination system (12) acts to permit the electrostatic deflection plates (13) to deflect drops (8) based on whether or not they contain the appropriate cell or other item. As a result, the flow cytometer acts to sort the cells by causing them to land in one or more collectors (14). Thus by sensing some property of the cells or other items the flow cytometer can discriminate between cells based on a particular characteristic and place them in the appropriate collector (14). In the system presently used to sort sperm, the X-bearing sperm droplets are charged positively and thus deflect in one direction, the Y-bearing sperm droplets are charged negatively and thus deflect the other way, and the wasted stream (that is unsortable cells) is uncharged and thus is collected in an undeflected stream into a suction tube or the like.

Figure 2:
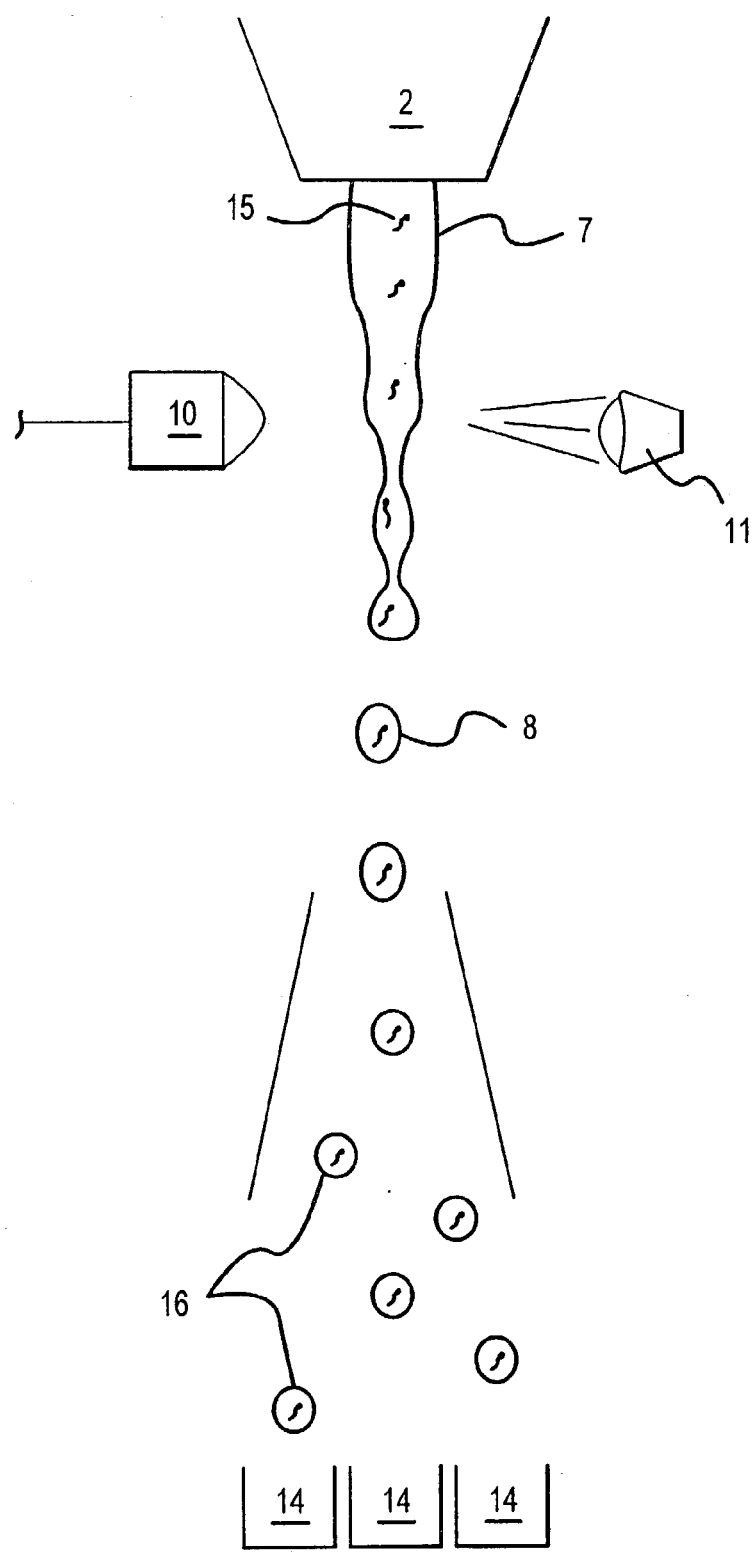

Referring to FIG. 2, the process can be even further understood. As shown in that figure, the nozzle (2) emits a stream (7) which because of the oscillator (6) (not shown in FIG. 2) forms drops (8). Since the cell source (1) (not shown in FIG. 2) may supply sperm cells (15) which have been stained according to the Johnson technique, the light stimulation by laser exciter (11) is differentially determined by sensor (10) so that the existence or nonexistence of a charge on each drop (8) as it separates from stream (7) can be controlled by the flow cytometer. This control results in positively charged, negatively charged, and uncharged drops (8) based upon their content. As shown in FIG. 2, certain drops are shown as deflected drops (16). These deflected drops (16) are those containing sperm cells (15) of the one or the other sex. They are then deposited in the appropriate collector (14) for later use.

One of the aspects of flow cytometry which is particularly important to its application for sperm sorting is the high speed operation of a flow cytometer. Advances have been particularly made by the flow cytometers available through Cytomation, Inc. under the MoFlo® trademark. These flow cytometers have increased sorting speeds extraordinarily and have thus made flow cytometry a technique which is likely to make feasible the commercial application of sperm sorting (among other commercial applications). They act to achieve high speed sorting, that is at a speed which is notably higher than those otherwise utilized. Specifically, Cytomation's MoFlo® flow cytometers act with oscillator frequencies of greater than about five kilohertz and more specifically can be operated in the 10 to 30 or even the 50 kilohertz ranges. Thus droplets are formed at very high frequencies and the cells contained within the sheath fluid environment can be emitted very rapidly from the nozzle (2). As a result, each of the components such as the nozzle (2) oscillator (6), and the like which make up and are part of a flow cytometer system result in a high speed cell sorter. In the application of a high speed cell sorter to the sorting of sperm cells, sorting at rates of greater than about 500 sorts per second is achieved. In fact, rates of sorting in the thousand and twelve hundred ranges have already been achieved through a high speed cell sorter. Importantly, it should be understood that the term "high speed" is a relative term such that as other advances in flow cytometry and specific applications are achieved, the aspect which is considered "high" may be varied or may remain absolute. In either definition, the general principle is that the sorting may occur at rates at which the parameters and physical characteristics of the flow cytometer are significant to the cells themselves when sorting particular cells such as sperm cells.

One aspect of high speed sorting which appears to come into play when sorting sperm cells is that of the pressures and other stresses to which the sperm cells are subjected within the flow cytometer. For instance, when operating at high speeds (and an alternative definition of "high speed"), flow cytometers can be operated at a pressure of 50 pounds per square inch and even 60 and higher pounds per square inch. These pressures may be considered high because they may result in effects upon the cells being sorted. The key as disclosed in the present invention for this facet is the fact that the stress thresholds of the particular cells are the determining factor. Additionally as further knowledge is gained it may be shown that the stress thresholds are a function of combined effects such as the particular species or the particular prior or subsequent handling of the cells. The key in this regard is that the stress imposed upon the cells can, in fact, alter their viability and their ability to achieve the desired result. In the pressure case, it may be that merely subjecting the sperm cells to a higher pressure as a result of the operation of the flow cytometer at that pressure may result in decreased performance of the cells. The present invention in one regard acts to minimize these stresses and thus results in greater efficacies as well as lower dosages as discussed later.

In considering the stress aspect of the cells, the present invention acts in a fashion which minimizes the stresses. These stresses can be minimized at any point in the over all cycle or process of collecting, sorting or even inseminating the animal. Importantly, the stress imposed by the handling of the cells within the flow cytometer appears significant for this application. In one embodiment of the invention, the sheath fluid is specifically selected so that it can serve in a coordinated fashion with both (or either) the pre-sort cell fluid environment or the post-sort cell fluid environment.

While naturally it is possible to adjust either the pre- or post-sort fluids, in one embodiment the invention adjusts the sheath fluid (3) so that it imposes significantly less stress upon the cells than was previously accomplished. In one regard the invention is remarkable in that it removes the total focus from that of operation of the flow cytometer to a focus on handling and removing stress from the cells themselves. For instance, while it has been known to utilize fluids having a proper pH factor or osmoality, the present invention recognizes that there may be certain chemical compositions to which the cells may be hyper-responsive. These hyper-responsive chemical compositions may naturally vary based upon the cells or even the prior handling of the cells. Importantly at present it appears that for sperm cells certain metabolic chemical compositions such as citrate seem to prevent unusually high stresses upon the cells. Thus, the hyper-responsive chemical compositions can be defined as those to which the cells are particularly responsive in the context of their functionality and the then-existing handling techniques. As to sperm cells it appears that metabolic compositions, specifically citrate constancy for bovine sperm cells and N-2-Hydroxyethylpiperazine-N'-2-ethane-sulfonic acid (HEPES) buffer constancy for equine sperm cells may be very important. Thus the present invention acts to minimize the changes through the type of operation or the selection of substances which may act as a means for minimizing the changes which the cells experience.

For the sheath fluid, a substance is selected according to one embodiment of the invention so that it may be chemically coordinated to prevent minimal changes. Thus, by selecting the appropriate sheath fluid not only in context of flow cytometry parameters, but rather also in context of the cell parameters themselves, the changes experienced by the cells and the over all result of the sorting can be enhanced. This is shown conceptually in FIG. 3. FIG. 3 shows some type of chemical factor (such as citrate or other factors) as it may exist throughout the various phases of the process. For instance, the four phases shown might represent the following: phase I may represent the existence of the cells within the cell source (1), phase II might show the existence of the cells as they are sorted in the sheath fluid environment, phase III might show the cells as they are collected after sorting and phase IV might show the reconstituted cells in a storage medium after sorting. These four phases as shown for the prior art may experience vastly different chemical factor environments. As shown conceptually, however, in the present invention the cells may experience very little change, most notably the dip or drop experienced between phases I and II may be virtually absent. This is as a result of the selection of the appropriate sheath fluid as mentioned above. Thus, as a result of being subjected to an appropriate sheath fluid, the cells in the present invention may experience a much lower level of stress.

One of the potential generalities that may exist with respect to this phenomenon is the fact that certain chemical compositions may represent more hyper-responsive chemical compositions than others. While naturally this may vary based upon the species of sperm, the handling, or even the type of cell involved, it appears that the viability of the cells for their intended purpose (here, artificial insemination) varies greatly, naturally or because of sorting or both, and so the cells exhibit a hyper-responsive character with respect to that chemical composition. By selecting certain metabolic chemical compositions, most notably citrates or chemicals which are within the citric acid cycle, great advances appear possible. Thus for the bovine sperm application, the sheath fluid (3) is selected and coordinated so that it presents about a 2.9 percent sodium citrate composition. Specifically, the 2.9 percent sodium citrate solution may be created as follows:
1. Place 29.0 grams of sodium citrate dihydrate ($Na_3C_6H_5O_7.2H_2O$) in a 1,000 ml volumetric flask
   a. Dissolve sodium citrate in ¾ of water batch, then add water to volume.
2. Add deionized or Nanopure water to make 1,000 ml final volume.
3. Transfer to bottles and autoclave at 15 lbs pressure (245° F.) for at least 30 minutes
   a. Autoclave solution using conditions to minimize evaporation (loose cover)
   b. Be careful that water does not boil away.
4. Cool slowly at room temperature.
5. Store sealed in a 5° C. cold room.
   Further, for a sheath fluid, the sodium citrate solution may be filtered.
6. Filter with a 0.22 micron filter using aseptic techniques.

Interestingly, for equine sperm cells such a composition does not perform as well. Rather, it has been discovered that for equine sperm cells, a HEPES buffered medium such as a HEPES bovine gamete medium—particularly HBGM3 as previously created by J. J. Parrish for a bovine application—works well. This medium is discussed in the article "Capacitation of Bovine Sperm by Heparin", 38 Biology of Reproduction 1171 (1988) hereby incorporated by reference. Not only is this surprising because it is not the same type of substance as is utilized for bovine sperm, but the actual buffer, originally was developed for a bovine application. Thus in the equine application the sheath fluid is selected which contains the HEPES buffer. This solution may have a pH at room temperature of about 7.54 (pH at 39° C.=7.4) with the following composition:

| Chemical | Dry weight (g/500 ml) |
| --- | --- |
| $CaCl_2$ | 0.145 |
| $KCl_2$ | 0.115 |
| $MgCl_2.6H_2O$ | 0.004 |
| $NaH_2PO_4.H_2O$ | 0.018 |
| NaCl | 2.525 |
| NaPyruvate | 0.011 |
| Lactic Acid (60%) | 1.84 ml |
| HEPES | 4.765 |
| $NaHCO_3$ | 0.420 |
| BSA (fraction V) | 3.0 |

One other aspect which may interplay in the present invention is the fact that the cells involved may experience unusual sensitivities. In one regard this may be due to the fact that sperm cells are in a class of cells which are non-repairing cells. That is, they do not have the ability to repair themselves and hence, they may need to be treated much more sensitively than is typical for flow cytometers or other handling equipment. Thus, it may be appropriate that the enhancement is particularly applicable when the flow cytometer acts to establish a source of sperm cells. Another potentially related aspect which may be unique to a class of cells such as sperm cells is the fact that their DNA is non-repairing, non-replicating, and non-transcribing. Either of these factors may come into play and so they may be relevant either individually or together. Thus, it may be that the teachings of the present invention apply to all gamete cells or even to viruses and the like which are non-repairing, non-translating, non-transcribing cells.

Figure 4:
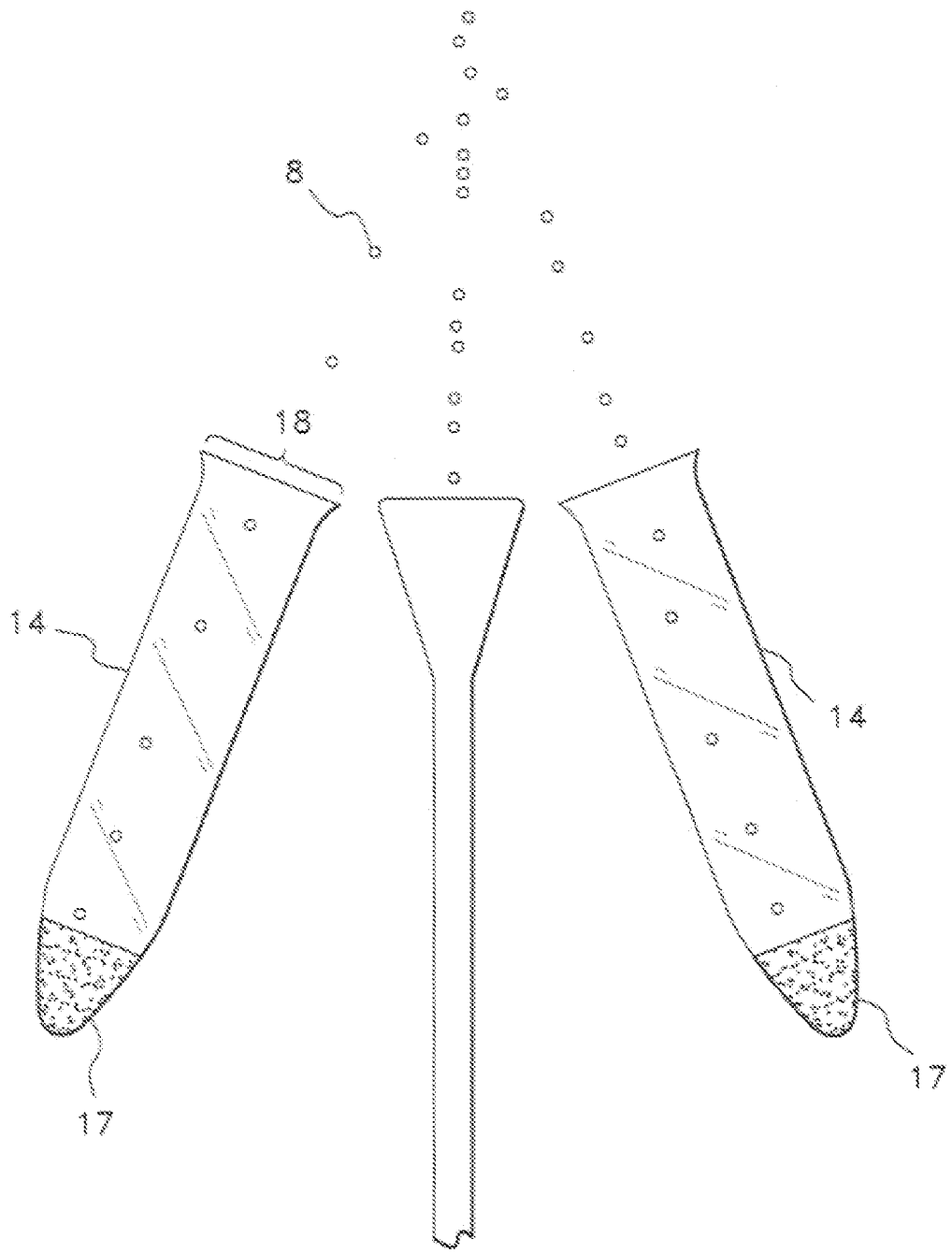

A separate aspect of the flow cytometer processing which may also be important is the fact of properly treating the cells both chemically and physically after they are sorted. As shown in FIG. 4, as the cells within drops (8) land in collector (14), it may be important that the container which makes up the collector be properly sized so that it acts as some means of avoiding an impact between the cells and the container itself. While it has been known to place an initial collector fluid (17) in the bottom of the container to collect the cells so that they do not hit the bottom of the container, it appears that a simple widening of the container to address variations in stream presentation as well as the inevitable splashing due to the impact of the cells into the container can be used to enhance the result. In one regard this can act as a cushioning element so that cells which may be mechanically delicate, that is, they may break or be damaged by an impact can be treated appropriately. Thus when the cytometer source establishes cells which are physically delicate cells as the cells to be sorted, it may be important to provide some type of cushioning element such as a wide collection tube for which the opening width (18) serves to position the walls of the container in a manner which avoids contact with the cells. Thus the tube does not present side walls so close that there is any significant probability of contact between those cells being sorted and the walls of the tube. In this manner, in addition to the collector fluid (17), it may be desirable to include a wide collection tube as well. Perhaps merely providing a wide opening to the container which serves as part of the collector (14) may be sufficient. For applications utilizing high speed sorting of sperm cells, it has been found that providing a container having an inner diameter opening of at least 15 millimeters is believed to be sufficient. Specifically when utilizing a 14 ml Falcon test tube in such an application, minimal physical damage to the cells as a result of the collector (14) has been discovered.

It should be noted that even the 14 ml Falcon test tube may not be optimum. Specifically, it is believed that designing a collection container which matches the geometry of the stream (that is, a "stream-matched container") may be most optimal. This stream-matched container may have any or all of the following characteristics: a relatively wide orifice, an elliptically shaped orifice, a lesser height to width ratio than currently involved, an angled or otherwise coordinated presentation such as may present side walls which are parallel to the falling streams, and the like. It may also be desirable to provide a mounting element such as a movable element or medium like ball bearings or the like to permit variable orientation of the tube to match the falling stream desired to be collected. In addition, the physical characteristics for the class of containers such as the existing tube (described as a "Falcon-type" test tube) may include not only the width of the tube but also the material (such polystyrene to which the cells do not stick) out of which it is made and the like. (These material options are well known for the 14 ml Falcon tube.) Thus the container and it collection fluid may also serve as a cushioning element to minimize physical damage to the cells. It also can serve, by its size, to facilitate collection of adequate numbers of sperm without a significant dilution effect.

Another aspect of the collector fluid (17) can be the fact that it, too, may serve to minimize chemical stresses upon the cells. In one regard, since it may be important to provide a nutrient to the cells both before and after sorting, the collector fluid (17) may be selected so as to provide a coordinated level of nutrient so that the levels are balanced both before and after sorting. For bovine sperm in which a nutrient of egg yolk citrate is utilized at a two percent egg yolk level, it has been discovered that utilizing a six percent egg yolk citrate level (that is six percent egg yolk content in a citrate solution) provides good results. This is as result of the volumes existing before and after the sorting event. The collector fluid (17) may start (before sorting) with about 2 ml of volume. The sorting event may add about double this volume (ending at three times the initial starting volume) with very little egg yolk citrate in solution (due to clogging and other flow cytometer considerations). Thus, the end result in terms of the level of the amount of egg yolk citrate present may be equivalent to the starting result, namely, two percent egg yolk content in a citrate solution due to the volumes involved. Thus the collector fluid (17) may be selected so as to create an ending collector fluid environment which is balanced with the initial nutrient or other fluid environment. In this manner, it may serve to minimize the time and changed level of composition to which the cells are subjected. Naturally, these fluid environments may be presented within the flow cytometer or may exist at some other prior time, the important point being merely minimizing the stress to which the cells are subjected at any time in their life cycle. Furthermore, since the initial chemical substance content can be varied (for instance the percent egg yolk content in the citrate may be varied up or down), likewise the starting collection fluid environment or various volumes may also be varied so that the ending result is the same. Thus, prior to commencing the sorting process, the collector fluid exists with a six percent egg yolk content in the citrate solution and after completion of the sorting event the collector fluid—with the sex-specific sperm—may result in a two percent egg yolk content in the citrate solution similar to the initial nutrient content.

Note that in later use these sperm cells may be treated to a 20% egg yolk content in the citrate fluid for other reasons, however these changes are not deemed to provide stress to the cells as they are merely a known part of the total insemination process. While naturally the levels may be varied as those skilled in the art readily understand, a 20% egg yolk citrate buffer may be constituted as follows:

I. Final Composition:
  80% sodium citrate solution (72 mM)
  20% (vol/vol) egg-yolk II. Preparation for 1 Liter:
  A. Sodium citrate solution
    1. Place 29.0 grams of sodium citrate dihydrate ($Na_3C_6H_5O_7 \cdot 2H_2O$) in a 1,000 ml volumetric flask
    2. Add deionized or Nanopure water to make 1,000 ml final volume.
    3. Transfer to bottles and autoclave at 15 lbs pressure (245° F.) for at least 30 minutes.
      a. Autoclave solution using conditions to minimize evaporation (loose cover)
      b. Be careful that water does not boil away.
    4. Cool slowly at room temperature.
    5. Store sealed in a 5° C. cold room.
  B. Egg preparation
    1. Obtain fresh hen's eggs from a good commercial source.
    2. Wash the eggs free of dirt (do not use too much detergent) and rinse.
    3. Immerse eggs in 70% ethanol for 2–5 minutes.
    4. Remove eggs and allow to dry (or wipe dry) and store on a clean towel.
  C. Preparation of extender
    1. Use sterile, clean glassware
    2. A-fraction (non-glycerol fraction)
      a. Place 800 ml of 2.9% sodium citrate solution in a 1,000 ml graduated cylinder.
      b. Antibiotic levels for the non-glycerol containing fraction (A-fraction) of the extender may be as follows:
        I. Tylosin=100 µg/ml
        ii. Gentamicin=500 µg/ml
        iii. Linco-spectin=300/600 µg/ml
      c. Add 200 ml of fresh egg-yolk as outlined below (Section D)
        I. Mix very thoroughly.
      d. This provides A-fraction extender based on 2.9% sodium citrate, with 20% egg-yolk and antibiotics at concentrations known to be non-toxic to bull sperm.
      e. Extender can be stored overnight at 5° C.
      f. Decant supernatant (upper 800 ml) the next day.
      g. Warm to 37° C. prior to use the next day.
  D. To add egg-yolk to a buffered solution, the following procedure works well.
    1. Wash egg and clean the eggs (see B above)
    2. Open egg and separate yolk from albumin using a yolk separator. Alternatively, pour yolk back and forth 2–3 times between the two half shells. Do not rupture the membrane around the yolk.
    3. Place the yolk onto a sterile piece of 15 cm filter paper.
    4. Hold the filter paper over the graduated cylinder containing buffer and squeeze the yolk (rupturing the membrane) and allow the yolk to run out of the golded filter paper into the cylinder. Typically about 12–15 ml of the yolk can be obtained from one egg.

Another aspect which may interplay in the various factors of the present invention is that of utilizing low dose amounts of sperm for artificial insemination or the like. Additional background on the aspect of sexed, artificial insemination may be found in "Prospects for Sorting Mammalian Sperm" by Rupert P. Amman and George E. Seidel, Jr., Colorado Associated University Press (1982) hereby incorporated by reference. As mentioned, natural insemination involves numbers of sperm on the order of billions of sperm. Typical artificial insemination is presently conducted with millions of sperm for bovine species and hundreds of millions of sperm for equine species. By the term "low dose" it is meant that the dosage of sperm utilized in the insemination event are less than one-half or preferably even less than about 10% of the typical number of sperm provided in a typical artificial insemination event. Thus, the term "low dose" is to be viewed in the context of the typical artificial insemination dosage or also as an absolute number. For bovine sperm where currently 1 to 10 million sperm are provided, a low dose process may be considered an absolute number of about 500,000 sperm or perhaps as low as 300,000 sperm or lower. In fact, through utilization of the techniques of the present invention, artificial insemination with good percentages of success has been shown with levels of insemination of sperm at 100,000 and 250,000 sperm (41% and 50%, respectively pregnancy rates). As shown in the article "Uterine Horn Insemination of Heifers With Very Low Numbers of Non-frozen and Sexed Spermatozoa" as published in 48 Theriogenology 1255 (1997) hereby incorporated by reference. Since sperm cells appear to display a sensitivity to dilution, these results may display particular interdependence on the utilization of low dose sperm samples with regards to various techniques of the present invention. The absolute numbers may be species dependent, for equine species, merely less than about ten, five, or even one million sperm may be considered a low dose process.

Another aspect which may be important is the fact that the sperm sexed through the present invention techniques is utilized in an artificial insemination system. Thus, when the collector (14) is used to provide sperm for artificial insemination the techniques of the present invention may be particularly relevant. Further, it is possible that the combination of both artificial insemination use and the use in a low dose environment may together create synergies which makes the various techniques of the present invention particularly appropriate. Naturally, the sexed sperm can be utilized not just in an artificial insemination mode, but in other techniques such as in vitro fertilization and the like.

The process of collecting, sorting, and eventually inseminating an animal through the use of flow cytometry involves a variety of steps. In the context of bovine insemination, first the semen is collected from the bull through the use of an artificial vagina. This occurs at rates of approximately 1.5 billion sperm per ml. This neat semen may be checked through the use of a spectrophotometer to assess concentration and may be microscopically evaluated to assure that it meets appropriate motility and viability standards. Antibiotics may then added. As a result the initial sample may have approximately 60 to 70 percent of the progressively motile sperm per ejaculate. For processing, a dilution through of some type TALP (tyrode albumin lactate pyruvate) may be used to get the numbers of sperm at a manageable level (for flow analysis) of approximately 100 million per ml. The TALP not only nurtures the sperm cells, but it may make them hyper-activated for the staining step. Prior to staining, in some species such as the equine species, centrifugation may be accomplished. Staining may be accomplished according to a multi-stained or single-stained protocol, the latter, the subject of the Johnson Patent and related technology. The staining may be accomplished while also adjusting the extender to create the appropriate nutrient environment. In bovine applications this may involve adding approximately 20% egg yolk content in a citrate solution immediately after staining. Further, in staining the sperm cells, it has been discovered that by using higher amounts of stain than might to some extent be expected better results may be achieved. This high concentration staining may involve using amounts of stain in the tens of micro-molar content such as discussed in the examples below where 38 micromolar content of Hoechst 33342 stain was used.

After adding the stain, an incubation period may be used such as incubating at one hour at 34° C. to hasten the dye uptake with concentrations at about 100 million sperm cells per ml. Filtration may then be accomplished to remove clumps of sperm cells and then dilution or extending may or may not be accomplished to the desired sort concentration of approximately 100 million sperm cells per ml may be accomplished. Sorting according to the various techniques discussed earlier may then be accomplished from which sperm cells may be recovered in the collection phase. As mentioned earlier, the collection may result in samples with approximately 2% egg yolk citrate concentrate content (for bovine species). This sample may then be concentrated to about 3–5 million sperm cells per ml through the use of centrifugation after which the sheath fluid and preserving fluid may be removed. A final extension may then be accomplished with either 20% egg yolk citrate or a Cornell Universal Extender or the like. The Cornell Universal Extender may have the following composition for 1000 ml:

14.5 g sodium citrate dihydrate
2.1 g NaHCO$_3$
0.4 g KCl
3.0 g glucose
9.37 g glycine
0.87 g citric acid
For 20% egg-yolk using 800 ml of above preparation and may include about 200 ml of egg-yolk composition.

After this last extending, 3 to 5 million sperm per ml (for bovine species) may result. This sample may then be cooled to slow the sperm's metabolism and to permit use over longer periods of time. In the equine species the sample may then be used in oviductal or other insemination processes as those skilled in the art well understand. In bovine sperm, the sample may be diluted yet one more time to the desired dosage level. It has been discovered that dilution may create an effect upon the sperm cell's viability and so it may be appropriate to avoid too large a level of dilution by providing a smaller sample. At present, low dosages of approximately 300,000 sperm per 0.184 ml may be achieved. Furthermore, it may be desirable to maintain a level of seminal plasma at approximately a five percent level, although the results of this requirement are, at present, mixed. The sperm cell specimen may then be placed in a straw for use in artificial insemination and may be transported to the cows or heifers to be inseminated.

In order to achieve conveniently timed artificial insemination, heifer or cow estrus may be synchronized using known techniques such as the utilization of prostaglandin F2$_\alpha$ according to techniques well known in the art. This latter substance may be particularly valuable in that it has been reported to potentially achieve enhanced fertility in heifers as discussed in the article "Prostoglandin F2$_\alpha$—A Fertility Drug in Dairy Cattle?", 18 Theriogenology 245 (1982) hereby incorporated by reference. While recent results have not maintained this premise, it may be that the present invention demonstrates its particular viability in situations of sexed, low dose insemination. For bovine species, artificial insemination may then be accomplished through the use of embryo transfer equipment with placement of the sperm cells deep within the uterine horns. This may be accomplished not at the peak moment as typically used in artificial insemination, but rather at a somewhat later moment such as 12 hours after that time since there is some possibility that fertility for sexed artificial insemination may occur slightly later. The utilization of embryo transfer equipment may be used because there may be high sensitivity of the uterine wall for such low dose, sexed inseminations.

Interestingly, rather than inseminating within the uterine body where such insemination are usually placed, by insemination deep within the uterine horn, better results may be achieved. Perhaps it is also surprising that the samples thus far studied have shown no difference between ipsi- and contra-lateral inseminations when accomplished deep within the uterine horn. By deep, it should be understood that the insertion is placed well into the uterine horn using the embryo transfer equipment. The fact that results do not appear significantly different using ipsi- and contra-lateral inseminations has led the present inventors to propose the use of insemination in both so that the process of identifying the appropriate uterine horn may no longer be needed.

As a result of the insemination, it is of course desired that an animal of the desired sex be produced. This animal may be produced according to the systems discussed earlier through the use of the sexed sperm specimen. It should also be understood that the techniques of the present invention may find application in other techniques such as laproscopic insemination, oviductal insemination, or the like.

As examples, the following experiments have been conducted. While not all use every aspect of the inventions described here, they do show the performance enhancements possible through differing aspects of the invention. Further, a summary of some experiments is contained in the article "Uterine Horn Insemination of Heifers With Very Low Numbers of Non-frozen and Sexed Spermatozoa" as referenced earlier. This article summarizes some of the data showing the efficacy of the present invention. As to the experiments, one has been conducted with sexed, unfrozen sperm cells with high success as follows:

EXAMPLE 1

Angus heifers, 13–14 mo of age and in moderate body condition, were synchronized with 25 mg of prostaglandin F-2 alpha at 12-day intervals and inseminated 6–26 h after observed standing estrus. Freshly collected semen from three 14–26 mo old bulls was incubated in 38 µM Hoechst 33342 at $75 \times 10^6$ sperm/ml in a TALP medium for 1 h at 34° C. Sperm were sorted by sex chromosomes on the basis of epiflourescence from laser excitation at 351 and 364 nm at 150 mW using a MoFlo® flow cytometer/cell sorter operating at 50 psi and using 2.9% Na citrate as sheath fluid. X chromosome-bearing sperm (~90% purity as verified by resorting sonicated sperm aliquots) were collected at ~500 live sperm/sec into 2-ml Eppendorf tubes containing 100 µl Cornell Universal Extender (CUE) with 20% egg yolk. Collected sperm were centrifuged at 600×g for 10 min and resuspended to $1.63 \times 10^6$ live sperm/ml in CUE. For a liquid semen unsexed control; Hoechst 33342-stained sperm were diluted with sheath fluid to $9 \times 10^5$ sperm/ml and centrifuged and resuspended to $1.63 \times 10^6$ progressively motile sperm/ml in CUE. Sexed semen and liquid control semen were cooled to 5° C. over 75 min and loaded into 0.25-ml straws (184 µl/straw). Straws were transported at 3 to 5° C. in a temperature-controlled beverage cooler 240 km for insemination 5 to 9 h after sorting. Sexed semen and liquid control semen were inseminated using side-opening blue sheaths (IMV), one half of each straw into each uterine horn ($3 \times 10^5$ live sperm/heifer). As a standard control, semen from the same bulls had been frozen in 0.5-cc straws by standard procedures (mean $15.6 \times 10^6$ motile sperm/dose post-thaw), thawed at 35° C. for 30 sec, and inseminated into the uterine body. Treatments were balanced over the 3 bulls and 2 inseminators in a ratio of 3:2:2 inseminations for the sexed semen and two controls. Pregnancy was determined ultrasonically 31–34 days after insemination and confirmed 64–67 days later when fetuses also were sexed (blindly). Data are presented in the table.

| Treatment | No. Heifers bred | No. Pregnant d31–34 | No. Pregnant d64–67 | No female fetuses |
|---|---|---|---|---|
| Sexed semen | 45 | 20 (44%) | 19 (42%) | 18 (95%)[a] |
| Liquid control | 28 | 15 (54% | 15 (54%) | 8 (53%)[b] |
| Frozen control | 29 | 16 (55%) | 15 (52%) | 12 (80%)[c] |

[a,b]Sex ratios of values with different superscripts differ (P < 0.02).

Although the pregnancy rate with sexed semen was only 80% of controls, this difference was not statistically significant (>0.1). One pregnancy was lost by 64–67d in each of the sexed and frozen control groups; 18 of 19 fetuses (95%) were female in the sexed group, and 20 of 30 (67%) were female in the control groups. The liquid semen control yielded a virtually identical pregnancy rate to the frozen semen control containing over 50 times more motile sperm (over 120 times more total sperm), demonstrating the efficacy of low-dose insemination into the uterine horns. We have altered the sex ratio in cattle significantly using flow cytometer technology and artificial insemination.

Similarly, an experiment was conducted with unsexed, unfrozen sperm cells and may be reported as follows:

EXAMPLE 2

The objective was to determine pregnancy rates when heifers are inseminated with extremely low numbers of frozen sperm under ideal field conditions. Semen from three Holstein bulls of above average fertility was extended in homogenized milk, 7% glycerol (CSS) extender plus 5% homologous seminal plasma to $2 \times 10^5$, $5 \times 10^5$ or $10 \times 10^6$ (control) total sperm per 0.25 ml French straw and frozen in moving liquid nitrogen vapor. Semen was thawed in 37° C. water for 20 sec. Holstein heifers 13–15 mo of age weighing 350–450 kg were injected with 25 mg prostaglandin F-2-alpha (Lutalyse®) twice at a 12-day interval and inseminated with an embryo transfer straw gun and side-opening sheath, half of the semen deep into each uterine horn 12 or 24 h after detection of estrus. The experiment was done in five replicates over 5 months, and balanced over two insemination technicians. Ambient temperature at breeding was frequently –10 to –20° C., so care was taken to keep insemination equipment warm. Pregnancy was determined by detection of a viable fetus using ultrasound 40–44 days post-estrus and confirmed 55–62 days post-estrus; 4 of 202 conceptuses were lost between these times. Day 55–62 pregnancy rates were 55/103 (53%), 71/101, (70%), and 72/102 (71%) for $2 \times 10^5$, $5 \times 10^5$ and $10 \times 10^6$ total sperm/inseminate (P<0.1). Pregnancy rates were different (P<0.05) among bulls (59, 62, and 74%), but not between technicians (64 and 65%) or inseminations times post-estrus (65% for 12 h and 64% for 24 h, N=153 at each time). With the methods described, pregnancy rates in heifers were similar with $5 \times 10^5$ and $10 \times 10^6$ total sperm per inseminate.

Prior a experiment has also been conducted on sexed, unfrozen sperm cells and may be reported as follows:

EXAMPLE 3

Semen was collected from bulls at Atlantic Breeders Cooperative, diluted 1:4 with a HEPES-buffered extender+0.1% BSA, and transported 160 km (~2 HR) to Beltsville, Md. where it was sorted at ambient temperature by flow cytometry into a TEST yield (20%) extender using methods described previously (Biol Reprod 41:199). Sorting rates of up to $2 \times 10^6$ sperm of each sex per 5–6 h at ~90% purity were achieved. Sperm were concentrated by centrifugation (300 g for 4 min) to $2 \times 10^6$ sperm/ml. Some sperm were sorted into extender containing homologous seminal plasma (final concentration, 5%). Sorted sperm were shipped by air to Colorado (~2,600 km) and stored at either ambient temperature or 5° C. (cooled during shipping over 6 hr in an Equitainer, an insulated device with an ice-containing compartment). Heifers or dry cows detected in estrus 11 to 36 h earlier were inseminated within 9 to 29 h of the end of the sperm sorting session. Sperm (1 to $2\times10^5$ in 0.1 ml) were deposited deep in the uterine horn ipsilateral to the ovary with the largest follicle as determined by ultrasound at the time of insemination.

None of 10 females became pregnant when inseminated with sperm shipped and stored at ambient temperature. Of 29 females inseminated with sperm cooled to 5° C. during shipping, 14 were pregnant at 4 weeks of gestation, and 12 (41%) at 8 weeks. Eleven of the 22 inseminated within 10 h of the end of sorting were pregnant at 8 weeks, but only 1 of 7 inseminated 17–24 h after sorting was pregnant. There was no significant effect of adding seminal plasma. One of the 12 fetuses was not of the predicted sex, one was unclear, and 10 were of the predicted sex, as determined by ultrasonography at 60–70 days of gestation.

Subsequently, 33 additional heifers were inseminated with 0.05 ml (semen extended as described above) into each uterine horn without using ultrasonography; only 3 were pregnant 4 weeks after insemination, and only 1 remained pregnant at 8 weeks. However, different bulls were used from the previous group, and all inseminations were done 18–29 h post-sorting. An additional 38 heifers were inseminated similarly (~22 h post-sorting) 200 km from our laboratory with sorted sperm from another bull; none of these was pregnant 8 weeks after insemination.

To summarize, it is possible to achieve pregnancies in cattle via artificial insemination of sperm sorted for sex chromosomes by flow cytometry, and the sex ratio of fetuses approximates that predicted by reanalysis of sorted sperm for DNA content (90%). However, pregnancy rates varied greatly in these preliminary experiments which required shipping sperm long distances. Fertility decreased drastically by 17 h post-sorting, but there was some confounding because different bulls were used at the different times. Further studies are needed to determine whether variation observed in pregnancy rates was due to bull differences, insemination techniques, interval between sorting and insemination, or other factors.

Finally, an experiment also has been conducted with unsexed, unfrozen sperm cells and may be reported as follows:

EXAMPLE 4

The objective was to determine pregnancy rates when heifers were inseminated with very low numbers of sperm under ideal experimental conditions. Semen from three Holstein bulls was extended in Cornell Universal Extender plus 5% homologous seminal plasma to $1\times10^5$ or $2.5\times10^5$ sperm per 0.1 ml; $2.5\times10^6$ total sperm per 0.25 ml was used as a control. Fully extended semen was packaged in modified 0.25 ml plastic French straws to deliver the 0.1 or 0.25 ml inseminate doses. Semen was cooled to 5° C. and used 26–57 h after collection. Holstein heifers 13–15 mo of age weighing 350–450 kg were injected with 25 mg prostaglandin F-2 alpha (Lutalyse®) at 12-day intervals and inseminated with an embryo transfer straw gun and side-opening sheath into one uterine horn 24 h after detection of estrus. Insemination was ipsilateral to the side with the largest follicle determined by ultrasound 12 h after estrus; side of ovulation was verified by detection of a corpus luteum by ultrasound 7–9 days post-estrus. Pregnancy was determined by detection of a fetus by ultrasound 42–45 days post estrus. The experiment was done in four replicates and balanced over three insemination technicians. Side of ovulation was determined correctly in 205 of 225 heifers (91%); surprisingly, pregnancy rates were nearly identical for ipsilateral and contralateral inseminates. Pregnancy rates were 38/93 (41%), 45/87 (52%), and 25/45 (56%) for $1\times10^5$, $2.5\times10^5$ and $2.5\times10^6$ sperm/-inseminate (P>0.1). There was a significant difference in pregnancy rate (P<0.05) among technician, but not among bulls. With the methods described, it may be possible to reduce sperm numbers per inseminate sufficiently that sperm sorted by sex with a flow cytometer would have commercial application.

As mentioned and as can be seen from the various experiments, the field is statistically based and thus a variety of additional experiments may be conducted to show the appropriate combination and limitation strategies. Thus synergies among various affects will further be identified, such as instances in which the dye effects and combined dye effects with laser excitation may be studied.

The discussion included in this application is intended to serve as a basic description. The reader should be aware that the specific discussion may not explicitly describe all embodiments possible; many alternatives are implicit. It also may not filly explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which may be submitted. It should be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

In addition, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. As but one example of this aspect, the disclosure of a "collector" should be understood to encompass disclosure of the act of "collecting"—whether explicitly discussed or not—and, conversely, were there only disclosure of the act of "collecting", such a disclosure should be understood to encompass disclosure of a "collector." Such changes and alternative terms are to be understood to be explicitly included in the description.

Any references mentioned in the application for this patent as well as all references listed in any information disclosure filed with the application are hereby incorporated by reference; however, to the extent statements might be considered inconsistent with the patenting of this/these invention(s) such statements are expressly not to be considered as made by the applicant(s).

We claim:

1. A method of sorting cells comprising the steps of:
   a. establishing a cell source which supplies viable sperm cells to be sorted;
   b. establishing a sheath fluid to create a sheath fluid environment for said viable sperm cells;
   c. sensing a property of said viable sperm cells;
   d. discriminating between said viable sperm cells having a desired sex characteristic at a rate of at least about 1200 sorts per second; and
   e. collecting said viable sperm cells having the desired sex characteristic comprising the step of cushioning said cells from impact with a collection container.

2. A method of sorting cells as described in claim 1 wherein said step of establishing a sheath fluid to create a sheath fluid environment for said viable sperm cells comprises the step of establishing a sheath fluid to create a sheath fluid environment for said viable sperm cells at a pressure of at least about fifty pounds per square inch.

3. A method of sorting cells as described in claim 1 wherein said step of collecting comprises the step of collecting in an angled collector.

* * * * *